United States Patent [19]  [11] Patent Number: 5,449,740
Tan et al.  [45] Date of Patent: Sep. 12, 1995

[54] RESIN SYSTEMS DERIVED FROM INSITU-GENERATED BISDIENES FROM BIS-BENZOCYCLOBUTENE COMPOUNDS

[75] Inventors: Loon-Seng Tan; Fred E. Arnold, both of Centerville, Ohio

[73] Assignee: The University of Dayton, Dayton, Ohio

[21] Appl. No.: 119,014

[22] Filed: Nov. 10, 1987

Related U.S. Application Data

[63] Continuation-in-part of Ser. No. 861,020, May 8, 1986, Pat. No. 4,711,964.

[51] Int. Cl.$^6$ .................. C08G 73/10; C08G 69/00
[52] U.S. Cl. .................. 528/322; 528/170; 528/220; 528/321
[58] Field of Search .............. 528/322, 170, 220, 321

[56] References Cited

U.S. PATENT DOCUMENTS

| | | | |
|---|---|---|---|
| 4,540,763 | 4/1985 | Kirchhoff | 526/281 |
| 4,570,011 | 2/1986 | So | 560/8 |
| 4,622,375 | 11/1986 | Wong | 526/284 |
| 4,642,329 | 2/1987 | Kirchhoff et al. | 526/284 |
| 4,661,193 | 4/1987 | Kirchhoff et al. | 156/307.3 |
| 4,711,964 | 12/1987 | Tan et al. | 528/322 |
| 4,719,283 | 1/1988 | Bartmann | 528/322 |
| 4,730,030 | 3/1988 | Hahn et al. | 528/322 |

FOREIGN PATENT DOCUMENTS 86100718 1/1986 European Pat. Off. .

*Primary Examiner*—John Kight, III
*Assistant Examiner*—P. Hampton-Hightower
*Attorney, Agent, or Firm*—Richard A. Killworth; John D. Upham

[57] ABSTRACT

Resins are prepared by polymerization of compounds of the formula:

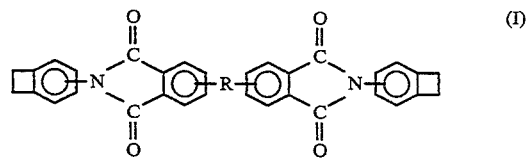

where R is a divalent linking group.

Blends of a compound of the formula (I) as defined above and a bis-maleimide of the formula:

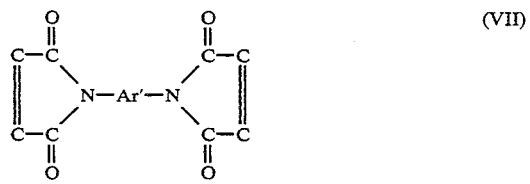

where Ar' is an aromatic linking group.

34 Claims, 9 Drawing Sheets

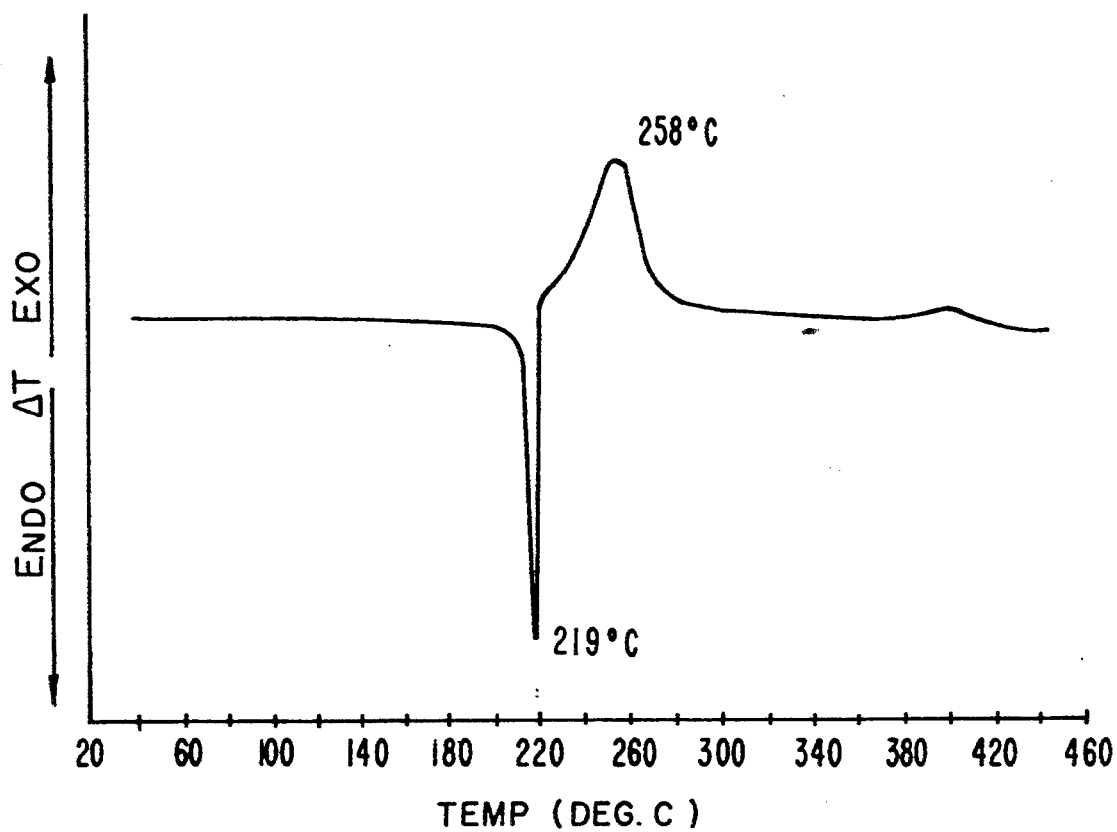
FIG. 1 DSC of 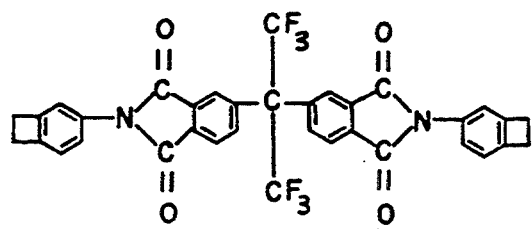

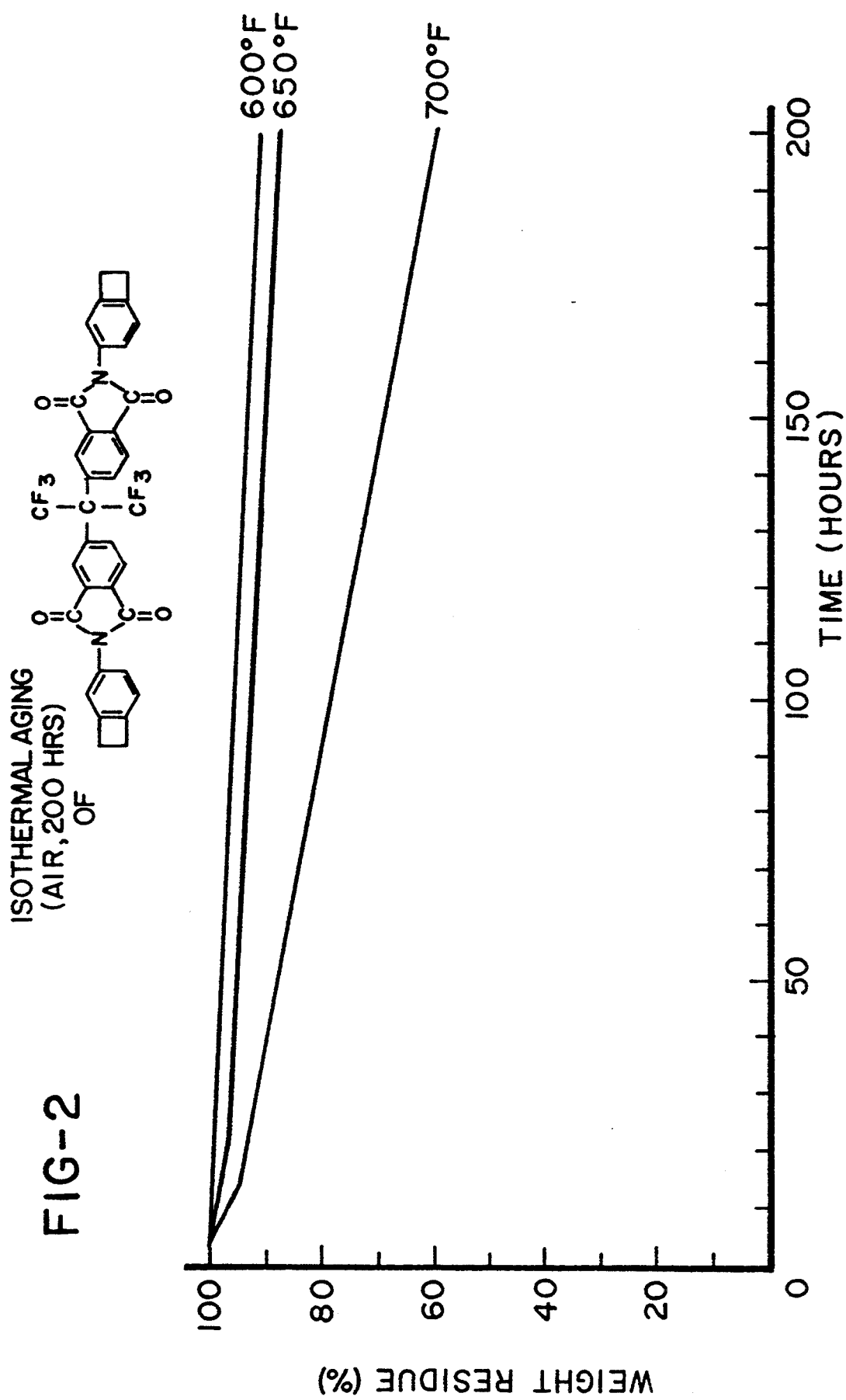

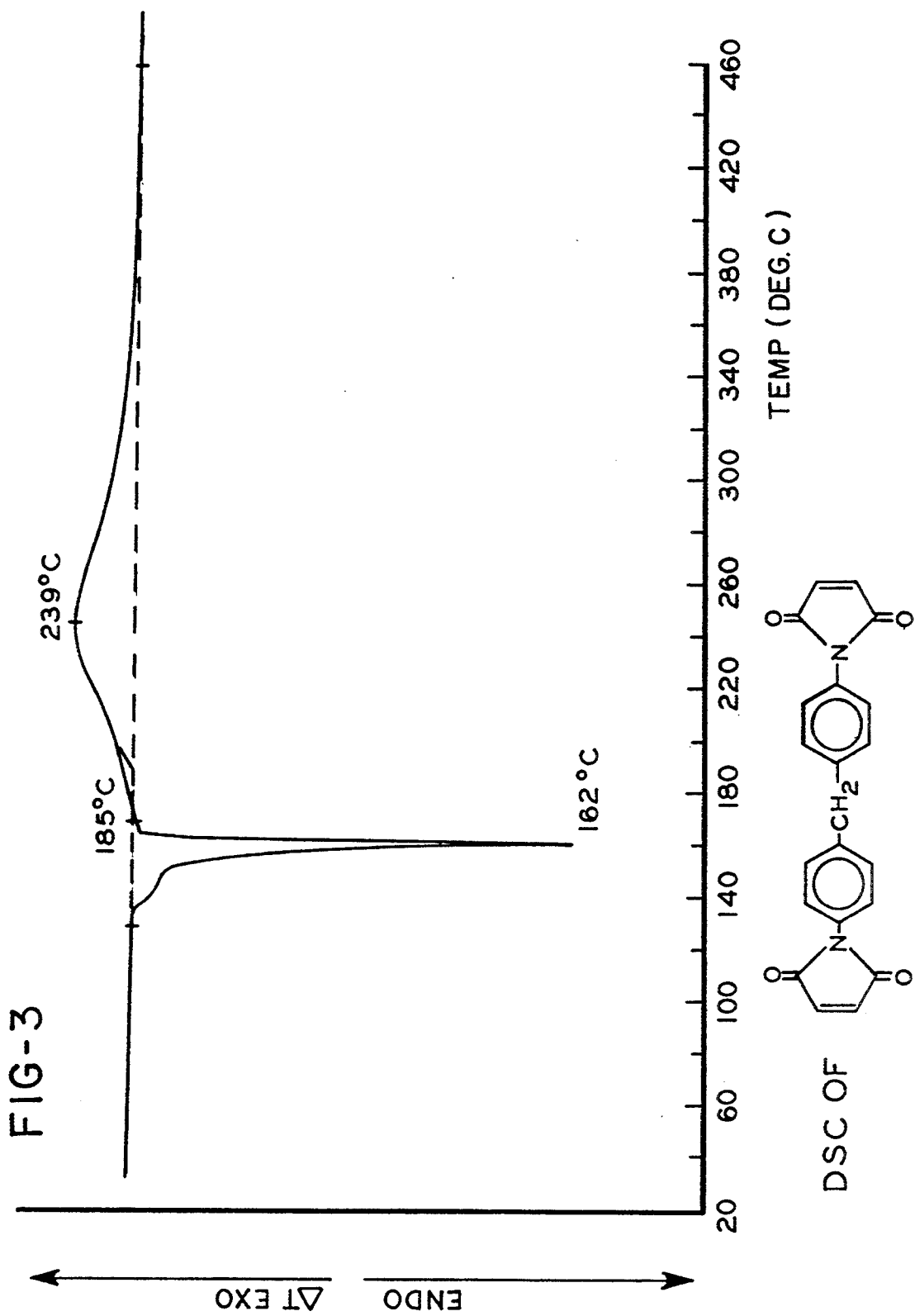

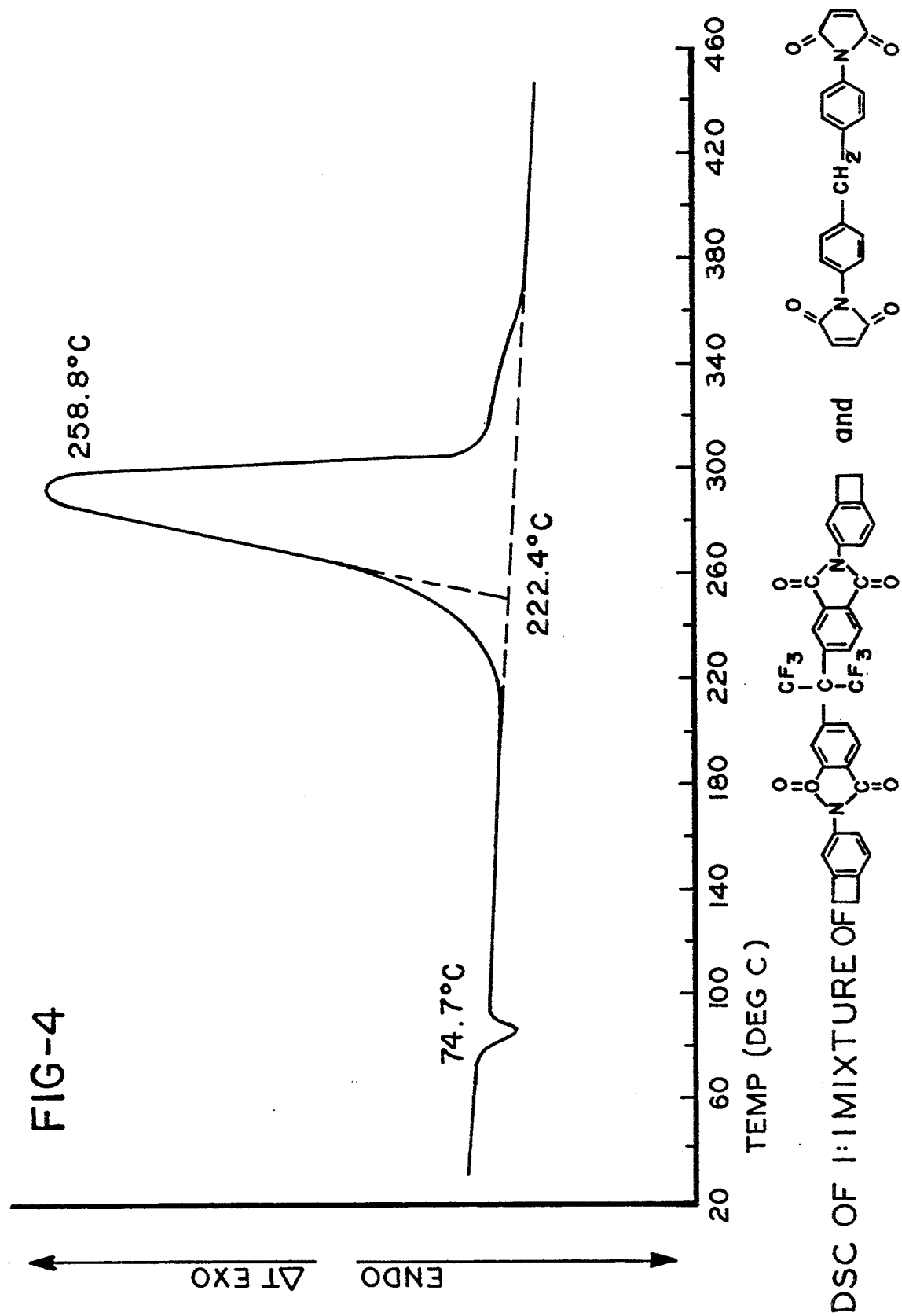

FIG-6
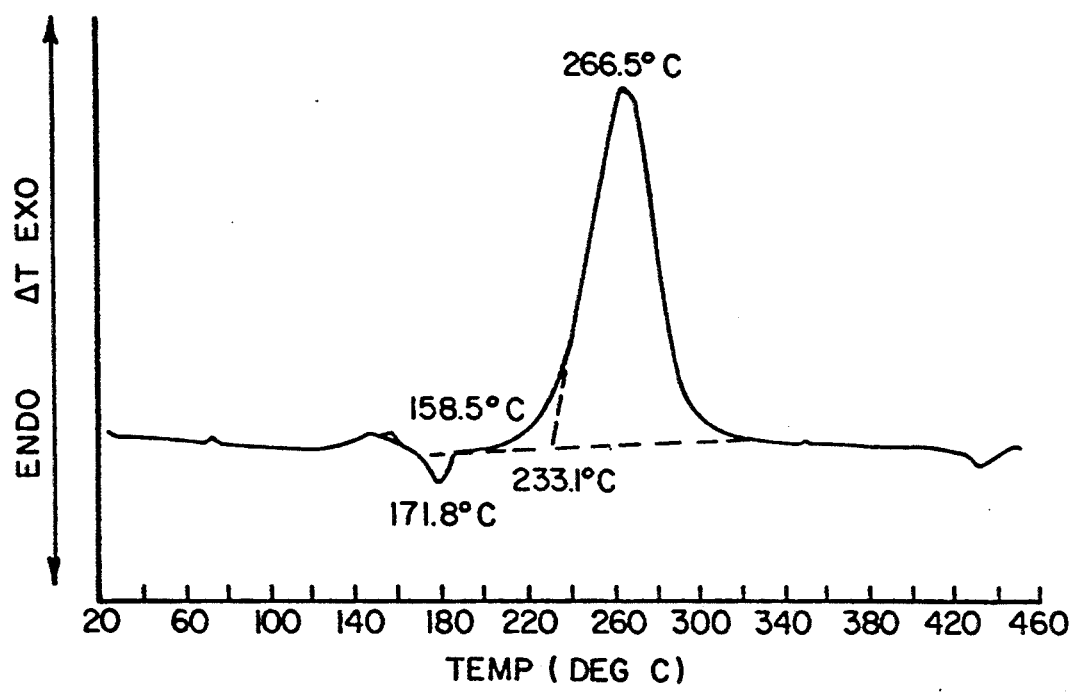
DSC OF 1:1 MIXTURE OF 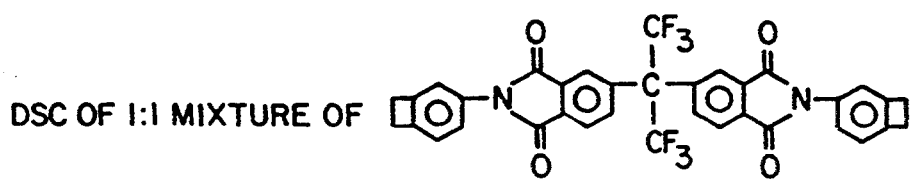
AND 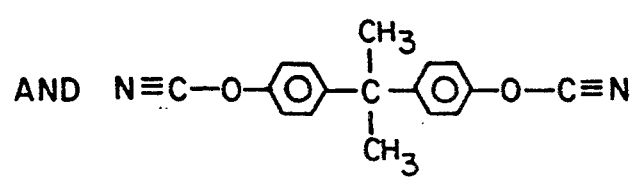

FIG-9
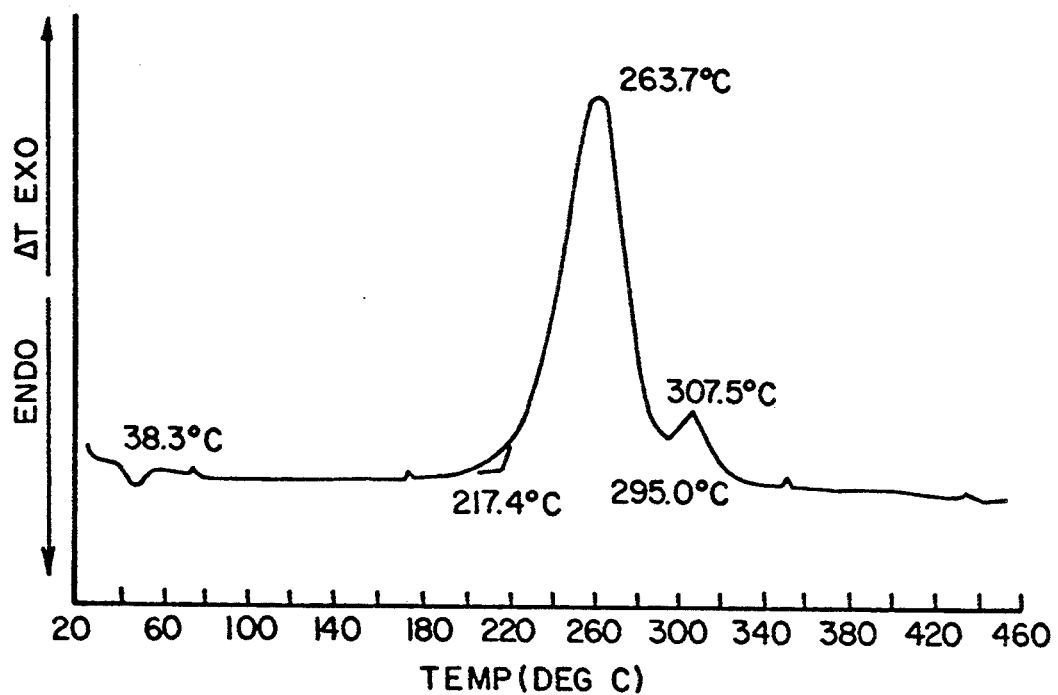
DSC OF 1:1 MIXTURE OF [structure] AND 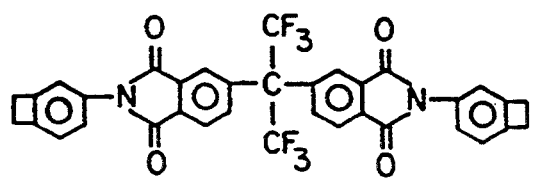

RESIN SYSTEMS DERIVED FROM INSITU-GENERATED BISDIENES FROM BIS-BENZOCYCLOBUTENE COMPOUNDS

GOVERNMENT RIGHTS

The U.S. Government has rights in this invention pursant to Contract No. F33615-84-C-5020 awarded by the Department of the Air Force.

CROSS-REFERENCE TO RELATED APPLICATIONS

This application is a continuation-in-part of U.S. patent application Ser. No. 861,020, filed May 8, 1986, now U.S. Pat. No. 4,711,964.

BACKGROUND OF THE INVENTION

The present invention relates to resins obtained by polymerization of compounds, and more particularly, to high temperature resistant thermoset resins obtained by polymerization of bis-benzocyclobutene compounds.

One form of a cycloaddition reaction is the Diels-Alder reaction in which an unsaturated group, a dienophile, combines with a 1,3-diene to form a six-membered ring. Benzocyclobutene functions very well in a Diels-Adler reaction. As taught by W. Oppolzer, *Synthesis* 793 (1978), under appropriate thermal conditions, the benzocyclobutene unit undergoes an electrocyclic ring opening to form the more reactive o-xylylene functionality. O-xylylene is a powerful diene, and thus, engages in a Diels-Alder reaction in the presence of a suitable dienophile. See Boekelheide, *Accounts Chem. Res.* 13, 65 (1980).

An example of a suitable dienophile is a bis-maleimide. Bis-maleimides are well-known as possessing strong dienophilicity. The dienophilic site, i.e., the carbon-carbon double bond, is not subjected to the substituent effect imposed by the rest of the structure. Thus, a bis-maleimide engages in a Diels-Alder polymerization in the presence of a suitable bisdiene such as bis (o-xylylene).

In the absence of a suitable dienophile, benzocyclobutene will react with itself. Although the exact cure mechanism for the bis-benzocyclobutene systems is still unclear, the results of studies in F. Jensen, W. Coleman, and A. Berlin, *Tet. Lett.* 15 (1962) and L. Errede, *J. Am. Chem. Soc.* 83, 949 (1961) suggest that at least two possible pathways exist: 1) cycloaddition and 2) linear addition. In the cycloaddition mode, an eight member ring is formed and incorporated into the highly aromatic skeleton. However, in the linear addition mode, a polymeric structure with a double strand of poly (o-xylylene) bridged by the aromatic imide groups results. It should be noted, however, that the terms "cycloaddition" and "linear addition" are used to describe the polymeric structures and do not implicate the mechanisms from which they arise.

Bis-benzocyclobutenes and polymers derived therefrom are disclosed in U.S. Pat. Nos. 4,540,763, 4,642,329 and 4,661,193. The bis-benzocyclobutenes are connected by direct bond or a bridging member such as a cyclic imido group. In general, the polymers are obtained by addition polymerization wherein the fused cyclobutene rings undergo thermal transformation to o-xylylene moieties which can react with one another.

U.S. Pat. No. 4,570,011 discloses a process for the preparation of an aromatic hydrocarbon with a cyclobutene ring fused thereto. U.S. Pat. No. 4,622,375 teaches copolymers of ethylene, propylene, and an olefinic benzocyclobutene monomer. European Patent Application 86100718.5 discloses Diels-Alder polymerization of benzodicyclobutenes with bismaleimides.

SUMMARY OF THE INVENTION

An object of the present invention is to provide compounds useful in the preparation of high temperature resistant thermoset resins.

A more particular object of the present invention is to provide high temperature resistant thermoset resins prepared by polymerization of bis-benzocyclobutene imide compounds.

An additional object of the present invention is to provide high temperature resistant thermoset resins which are useful in composite materials in the advanced aircraft and aerospace vehicles.

A further object of the present invention is to provide compounds which are polymerizable by Diels-Alder polymerization.

Another object of the present invention is to provide high temperature resistant thermoset resins prepared by Diels-Alder polymerization of bis-benzocyclobutene imide compounds with bis-maleimides, dicyanates, or bisphenylacetylenes.

The present invention provides compounds of the general formula:

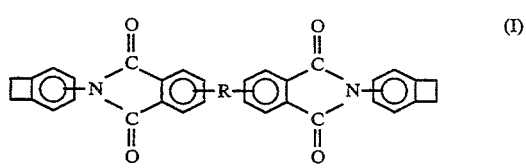
(I)

where R is a divalent linking group. Upon heating these compounds to about 200° C., the benzocyclobutene unit undergoes an electrocyclic ring-opening to form the more reactive o-xylylene functionality which is a powerful diene.

In accordance with the present invention, when suitable bisdienophiles are present, resins are obtained by Diels-Alder polymerization of bis-benzocyclobutene imide compounds with the bisdienophiles. When suitable bisdienophiles are absent, resins are obtained by the cycloaddition or linear addition polymerization of the bis-benzocyclobutene imide compounds with themselves. In the cycloaddition mode, an eight membered ring forms and is incorporated into the highly aromatic skeleton. In the linear addition mode, a polymeric structure with a double strand of poly (o-xylylene) bridged by the aromatic imide groups results.

In one embodiment, the compound is represented by the formula (Ia):

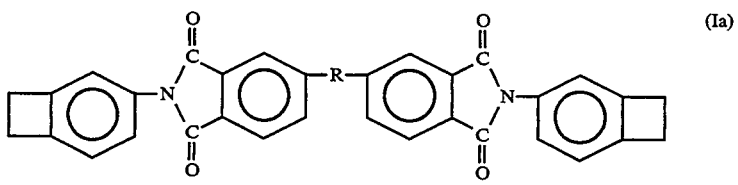
(Ia)

where R is a divalent linking group.

In the compound of formula (I) above, careful attention must be paid to the selection of the R-moiety. R is selected so as to maximize the thermooxidative stability of the resin. Isothermal aging studies indicate that as the structural rigidity of the R-moiety increases, the thermooxidative stability of the R-moiety increases. For example, when R is selected from the group consisting of the following, the increasing order of thermooxidative stability is:

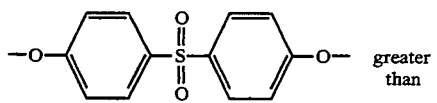 greater than

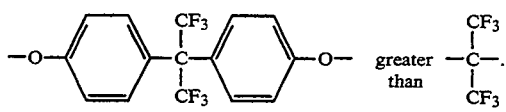 greater than $-\overset{CF_3}{\underset{CF_3}{C}}-$.

Thus, in a preferred embodiment, R is a perfluoro-aliphatic group such as —C(CF$_3$)$_2$—. In another embodiment, R is an aromatic linking group. In other applications where thermooxidative stability is not as critical, numerous R groups are useful in the compounds of the present invention.

In one embodiment, R is selected from the group consisting of —C(CH$_3$)$_2$—, —CH$_2$—, —O—, —S—, —CO—, —SO$_2$—, and a direct bond.

In another embodiment, R is represented by the formula (II):

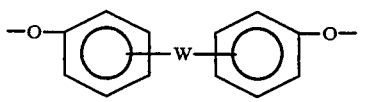
(II)

where W is selected from the group consisting of —C(CF$_3$)$_2$—, —C(CH$_3$)$_2$—, —CH$_2$—, —O—, —S—, —CO—, —SO$_2$—, and a direct bond.

In a more particular embodiment, R is represented by the formula (IIa):

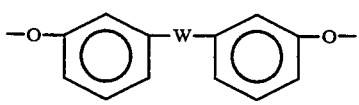
(IIa)

where W is as defined above.

In another embodiment, R is represented by the formula (III):

(III)

where X is selected from the group consisting of —C(CF$_3$)$_2$—, —C(CH$_3$)$_2$—, —CH$_2$—, —O—, —S—, —CO—, —SO$_2$—, and a direct bond.

In a more particular embodiment, R is represented by the formula (IIIa):

(IIIa)

where X is as defined above.

In an additional embodiment, R is represented by the formula (IV):

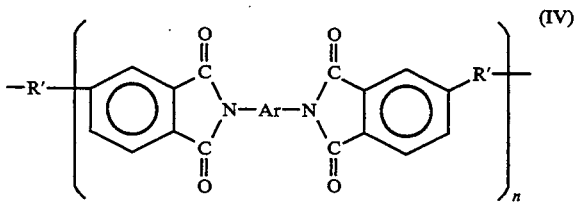
(IV)

where
R' is selected from the group consisting of —C(CF$_3$)$_2$—, —C(CH$_3$)$_2$—, —CH$_2$—, —O—, —S—, —CO—, —SO$_2$—, and a direct bond,
n is 1 to 4, and
Ar is an aromatic linking group such as a linking group selected from the group consisting of a meta phenylene group, a para phenylene group, and the formula (III) as defined above.

In accordance with the present invention, when suitable bisdienophiles are present, resins are obtained by Diels-Alder polymerization of the bis-benzocyclobutene imide compounds with the bisdienophiles. A suitable bisdienophile is a bis-maleimide. Thus, the present invention also provides blends of the aforementioned bis-benzocyclobutenes and bis-maleimides of the formula (VII):

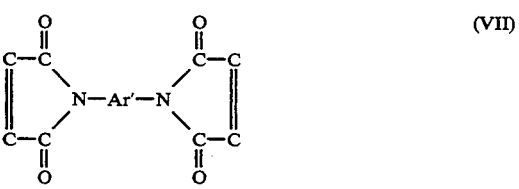
(VII)

where Ar' is an aromatic linking group.

In one embodiment, Ar' is an aromatic linking group such as a linking group selected from the group consisting of a meta phenylene group, a para phenylene group and the formula (III):

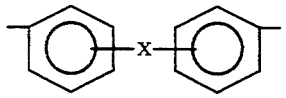
(III)

where X is selected from the group consisting of —C(CF$_3$)$_2$—, —C(CH$_3$)$_2$—, —CH$_2$—, —O—, —S—, —CO—, —SO$_2$—, and a direct bond.

Aromatic ether bis-maleimides are also useful as dienophiles in the present invention.

Another suitable bisdienophile is a dicyanate. Thus, the present invention also provides blends of the aforementioned bis-benzocyclobutenes and dicyanates of the formula (VIII):

N≡C—O—Ar"—O—C≡N    (VIII)

where Ar" is an aromatic linking group.

In one embodiment, Ar" is represented by the formula (IX):

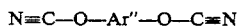
(IX)

where J is selected from the group consisting of —C(CF$_3$)$_2$—, —C(CH$_3$)$_2$—, —CH$_2$—, —O—, —S—, —CO—, and —SO$_2$—, or J represents a direct bond.

In another embodiment, Ar" is represented by the formula (X):

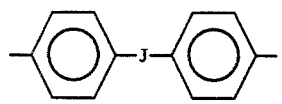
(X)

where L is selected from the group consisting of —C(CF$_3$)$_2$—, —C(CH$_3$)$_2$—, —CH$_2$—, —O—, —S—, —CO—, and —SO$_2$—, or L represents a direct bond.

In another embodiment, Ar" is a meta phenylene group.

Another suitable bisdienophile is a bisphenylacetylene. Thus, the present invention also provides blends of the aforementioned bis-benzocyclobutenes and bisphenylacetylenes of the formula (XI):

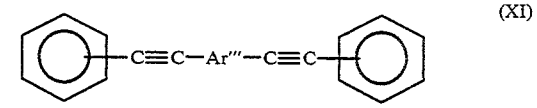
(XI)

where Ar'" is an aromatic linking group.

In one embodiment, Ar'" is represented by the formula (XII):

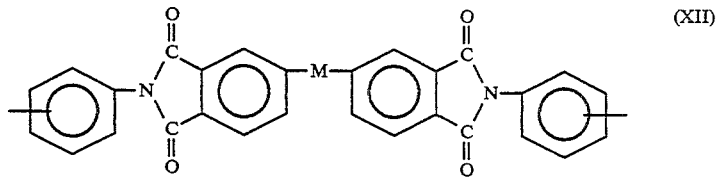
(XII)

where M is selected from the group consisting of —C(CF$_3$)$_2$—, —C(CH$_3$)$_2$—, —CH$_2$—, —O—, —S—, —CO—, and —SO$_2$—, or M represents a direct bond.

In another embodiment, Ar'" is represented by the formula (XIII):

(XIII)

where Q is selected from the group consisting of ortho phenylene, metal phenylene, or para phenylene.

Other objects and advantages of the invention will be apparent from the following description, the accompanying drawings, and the appended claims.

BRIEF DESCRIPTION OF THE DRAWINGS

FIG. 1 is a DSC (differential scanning calorimetry) curve of bis-2,2-(N-4-benzocyclobutenyl phthalimido)-hexafluoropropane;

FIG. 2 provides isothermal aging studies for bis-2,2-(N-4-benzocyclobutenyl phthalimido)hexafluoropropane;

FIG. 3 is a DSC of 1,1'-(methylene di-4,1-phenylene)-bis-maleimide;

FIG. 4 is a DSC of a resin which is a reaction product prepared by Diels-Alder polymerization of a 1:1 molar ratio of bis-2,2-(N-4-benzocyclobutenyl phthalimido)-hexafluoropropane with 1,1'-(methylene di-4,1-phenylene)bis-maleimide;

FIG. 6 is a DSC of a resin which is a reaction product prepared by Diels-Alder polymerization of a 1:1 molar ratio of 2,2-bis[4-(N-4-benzocyclobutenyl phthalimido)]hexafluoropropane with bisphenol A dicyanate;

FIG. 9 is a DSC of a resin which is a reaction product prepared by Diels-Alder polymerization of a 1:1 molar ratio of 2,2,-bis[4-(N-4-benzycyclobutenyl phthalimido)]hexafluoropropane with 1,1'-(1,3-phenylene)bis-(3-phenyl-2-propyn-1-one).

DETAILED DESCRIPTION OF THE INVENTION

Figure 5:
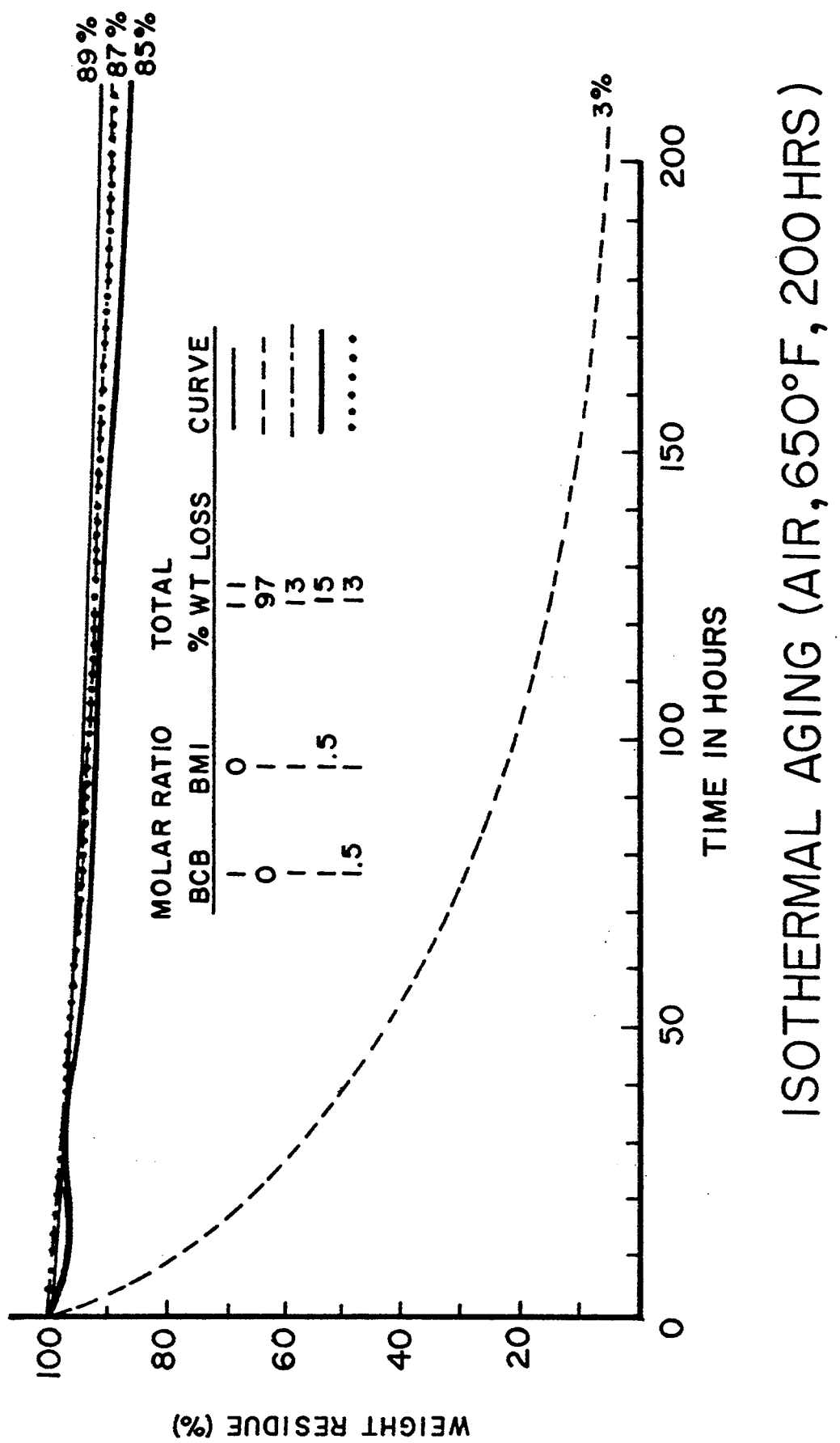
FIG. 5 provides isothermal aging studies for bis-2,2-(N-4-benzocyclobutenyl phthalimido)hexafluoropropane; 1,1'-(methylene di-4,1-phenylene)bis-maleimide; and resins prepared by Diels-Alder polymerization of different molar ratios thereof.

Bis-benzocyclobutene imide compounds useful in the present invention can be prepared by several synthesis schemes. In general, the compounds of the present invention are prepared by condensing 4-aminobenzocyclobutene with a dianhydride.

The following reaction scheme sets forth the synthesis of 4-aminobenzocyclobutene:

2185 (1964) while Step (D) is discussed in Horner and Schmelzer, *Chem Ber* 93, 1774 (1960).

The dianhydrides useful in preparing the compounds of the present invention are prepared in a conventional manner. For example, U.S. Pat. No. 4,196,277 discloses the preparation of 2,2-bis[4-(3,4-dicarboxyphenoxy)-phenyl]hexafluoropropane dianhydride (BFDA). Similarly, U.S. Pat. No. 3,812,159 discloses the preparation of 1,4-bis(3,4-dicarboxyphenoxy)diphenylsulfone dianhydride (BSDA).

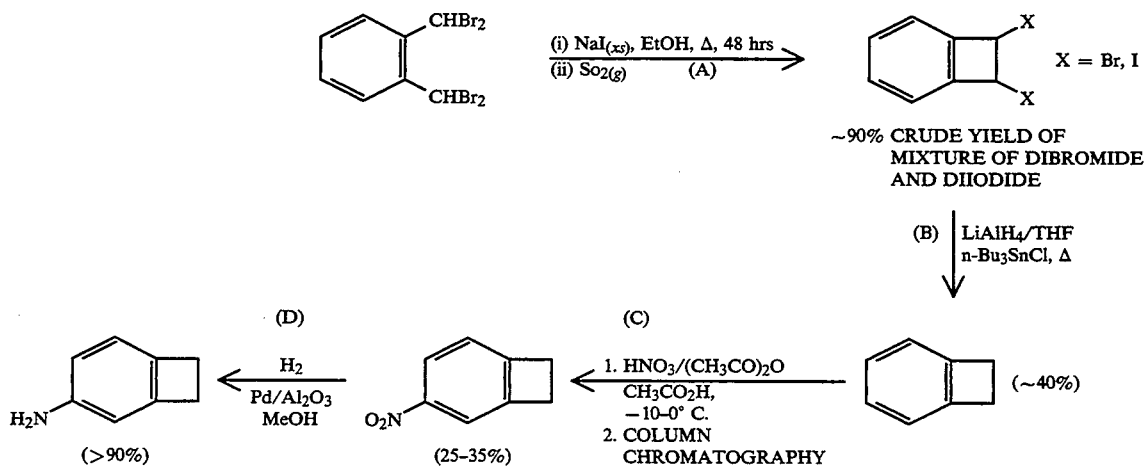

Step (A) is explained in Cava and Napier, *J. Am. Chem. Soc.* 79, 1701 (1957). Sanders and Giering, *J. Org. Chem.* 38, 3055 (1973) provides details on Step (B). Step (C) is discussed in Lloyd and Ongley, *Tetrahedron* 20, The following reaction scheme sets forth the general synthesis of certain bis-benzocyclobutene imides useful in the present invention.

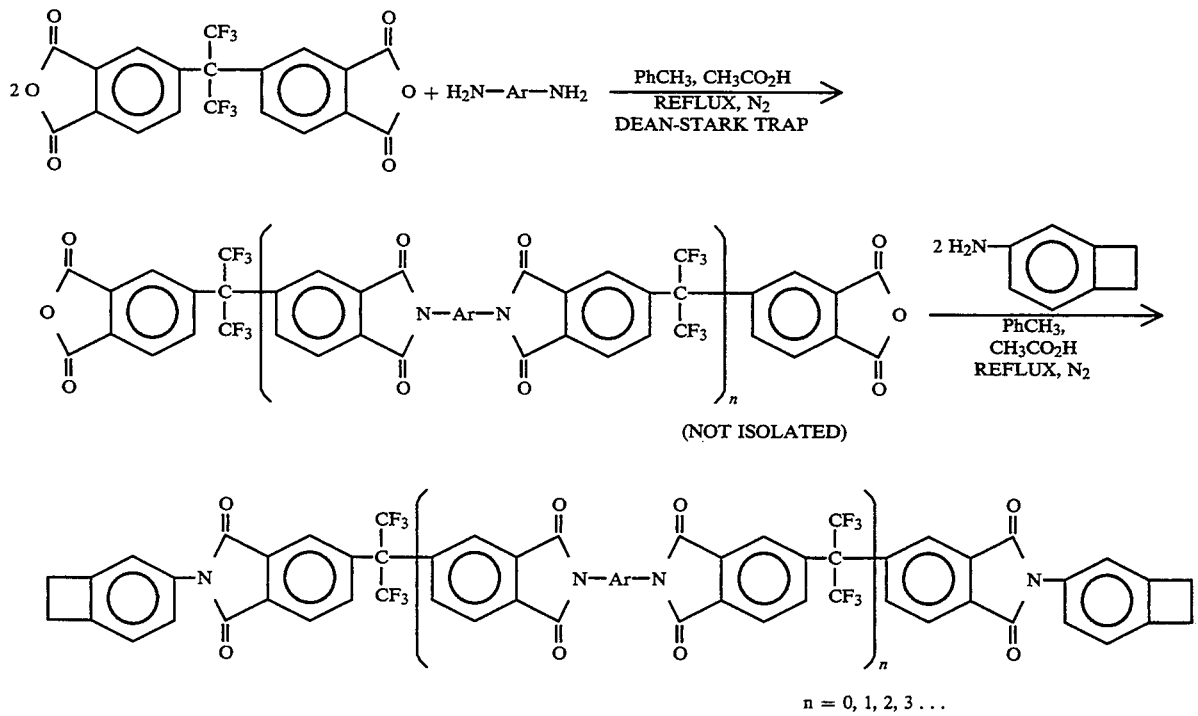

-continued
BISBENZOCYCLOBUTENE AROMATIC IMIDE OLIGOMERS

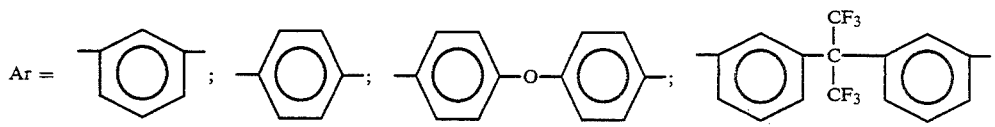

The preferred methods of preparation of certain bisbenzocyclobutene imides useful in the present invention are described in the Examples below.

In the absence of a suitable dienophile, the compound reacts with itself. Although the exact cure mechanism is unclear, studies suggest that at least two possible pathways exist: 1) cycloaddition and 2) linear addition.

Following the cycloaddition mode, a polymer including an eight membered ring of the formula (V):

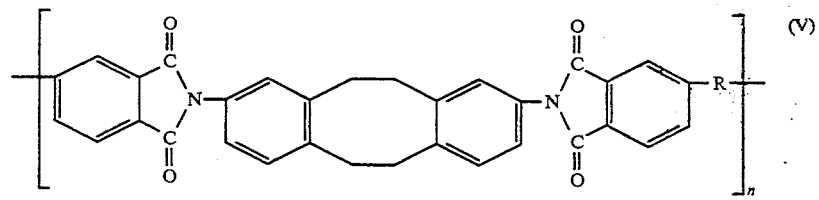

is believed to form where n is greater than or equal to 10 and is incorporated into the highly aromatic skeleton. In general, cycloaddition polymerization of the compounds occurs at a temperature of greater than about 200° C.

Following the linear addition mode, a polymeric structure of the formula (VI):

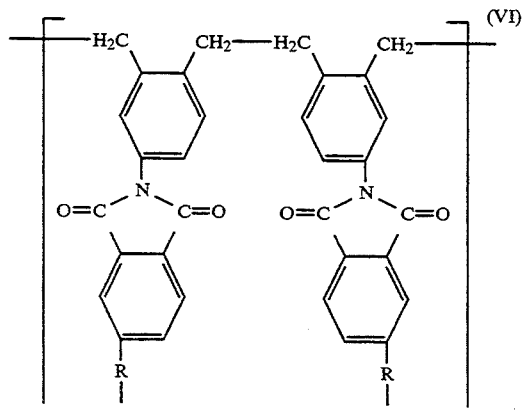

-continued

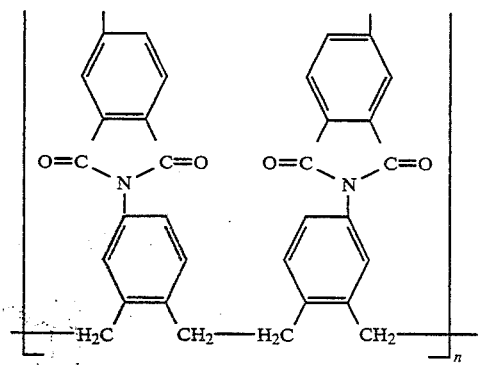

with a double strand of poly (o-xylylene) bridged by the aromatic imide groups is believed to result where n is greater than or equal to 10. In general, linear addition of the compounds occurs at a temperature of greater than about 200° C. The terms "cycloaddition" and "linear addition" are used to describe the structures and do not implicate the mechanisms from which they arise.

A Differential Scanning Calorimetric (DSC) study indicates the endothermic or exothermic nature of a reaction as the temperature increases. Typically, the reaction temperature is plotted on the abscissa while the temperature change is plotted on the ordinate. A DSC study is useful in the present invention because it indicates the exotherms for a given compound. For example, when R is —C(CF$_3$)$_2$— in the compound of formula (Ia) above, the DSC is represented by FIG. 1 which was run at a heating rate of 10° C. per minute. FIG. 1 shows a melting temperature of about 219° C. and a reaction exotherm of 258° C.

Table 1 sets forth thermal properties of compounds of formula (Ia):

TABLE 1

| | | | | | | ISOTHERMAL AGING |
| | | | Tpoly | | T$_g$ (CURE) | 200 HRS/AIR |
| Examples | T$_g$ | T$_m$ | ONSET | MAX | DSC | % WEIGHT LOSS |
|---|---|---|---|---|---|---|
| 1 | 116 | 219 | 230 | 258 | 281 | 9% (600° F.) |
| | | | | | | 13% (650° F.) |
| | | | | 404 | | 40% (700° F.) |
| 2 | 62 | — | 229 | 263 | 247 | 7% (600° F.) |
| | | | | 369 | (251) (TMA) | 25% (650° F.) |
| | | | 250 | 263 | | |
| 3 | 149 | 249 | | 357; | 240 | 10% (600° F.) |

TABLE 1-continued

THERMAL PROPERTIES OF COMPOUNDS OF FORMULA (Ia)

| Examples | $T_g$ | $T_m$ | Tpoly ONSET | Tpoly MAX | $T_g$ (CURE) DSC | ISOTHERMAL AGING 200 HRS/AIR % WEIGHT LOSS |
|---|---|---|---|---|---|---|
| | | | | 377 | | |

All Table 1 temperature values are expressed in °C. unless otherwise specified. The Example numbers correspond to the examples given below. Tg is the glass transition temperature of the compound while Tm is the melting temperature of the compound. Tpoly onset is the beginning polymerization temperature while Tpoly max is the temperature at which polymerization reaches its maximum. The second Tpoly max values represent small, secondary exotherms which were observed for both cured and uncured samples. Tg(cure) is the glass transition temperature of the polymer; the Tg(cure) measurements were made on samples previously cured under $N_2$ atmosphere at 250°-254° C. for 8 hours. TMA means determined by thermal mechanical analysis. The isothermal aging studies were carried out in circulating air for 200 hours at constant temperature as specified.

FIG. 2 represents isothermal aging studies of bis-2,2-(N-4-benzocyclobutenyl phthalimido)hexafluoropropane. The samples were cured as indicated above for Tg(cure). The isothermal aging studies were carried out by placing cured samples in a circulating air oven for 200 hours, and periodically measuring the change in weight. This data illustrates the high temperature utility of the compounds.

Table 2 sets forth thermal characteristics of compounds of formula (Ia) where R is represented by formula (IV) and R' is $-C(CF_3)_2-$:

carried out in circulating air for 200 hours at the temperature specified.

The cure mechanism for the bis-benzocyclobutene systems has a significant impact on the nature and properties of the resins prepared. In a preferred embodiment, the resins are useful in composite materials in the advanced aircraft and aerospace vehicles.

The resins of the present invention can be prepared by Diels-Alder polymerization of the particular compounds used if suitable dienophiles are present. Upon heating the compounds to 200° C., Diels-Alder polymerization occurs whereby the benzocyclobutene unit undergoes an electrocyclic ring opening to form the more reactive o-xylylene functionality wherein the o-xylylene functionality undergoes cycloaddition with the dienophile.

In general, Diels-Alder polymerization of the compounds occurs at a temperature of greater than about 200° C.

Dienophiles suitable for use in a Diels-Alder reaction are useful in the present invention. Examples of useful dienophiles include benzoquinones, bis-maleimides, dicyanates, bisphenylacetylenes, acrylic acid, and related compounds such as acrylonitrile and acrolein. Preferred dienophiles are bis-maleimides, dicyanates, and bisphenylacetylenes.

Bis-maleimides useful in the present invention can be

TABLE 2

THERMAL CHARACTERISTICS OF COMPOUNDS OF FORMULA (Ia) WHERE R IS REPRESENTED BY FORMULA (IV) AND R' IS $-C(CF_3)_2-$

| Examples | $T_g$ | $T_m$ | Curing Exotherm ONSET | Curing Exotherm MAX | $T_g$ (CURE) | | $T_{10\%}$ | ISOTHERMAL AGING 200 HR/AIR % WEIGHT LOSS |
|---|---|---|---|---|---|---|---|---|
| 1 | 116 | 219 | 232 | 258 | 281 | | 496 | 43% (700° F.) |
| 4 | 81 | — | 197 | 257 | 258 | | 470 | 12% (650° F.) |
| | | | | | 256 | (DSC) | | 43% (700° F.) |
| | | | | | 288 | | | |
| 7 | 81 | — | 210 | 254 | 314 | (TMA) | 500 | 12% (650° F.) |
| | | | | | 299 | (DSC) | | 24% (700° F.) |
| 6 | 78 | — | 208 | 254 | 289 | (DSC) | 519 | 35% (700° F.) |
| 5 | 81 | — | 213 | 252 | 282 | (DSC) | 518 | 41% (700° F.) |

All Table 2 temperature values are expressed in °C. unless otherwise specified. The Example numbers correspond to the examples given below. Tg is the glass transition temperature of the compound while Tm is the melting temperature of the compound. Curing exotherm onset is the beginning cure temperature while curing exotherm max is the maximum cure temperature. Also, small exotherms around 360°-380° C. were observed. Tg(cure) is the glass transition temperature of the polymer. The Tg(cure) values without (DSC) following were obtained by rescanning samples previously heated to 450° C. on a DSC; the Tg(cure) values with (DSC) or (TMA) following were obtained from samples previously cured at 250° C./8 hours/$N_2$. TMA means determined by thermal mechanical analysis. $T_{10\%}$ is the temperature at which a 10% weight loss of the sample was determined by thermal gravimetric analysis (TGA). The isothermal aging studies were prepared using fully conventional methods. The classic imidization reaction can be employed. For example, maleic anhydride can be reacted with the diamine corresponding to the final product bis-maleimide desired. Typically, the imidization is carried out in an inert aprotic solvent such as dimethylformamide, dimethylsulfoxide, or acetamide using a slight excess of maleic anhydride. Typical reaction temperatures are 40°-60° C. Typical reaction times are 1-1.5 hours.

Aromatic ether bis-maleimides are also useful in the present invention. As taught in U.S. Pat. No. 4,460,783, an ether imide can be prepared in a two step reaction. First, a diamine is contacted with an ethylenically unsaturated dicarboxylic acid anhydride in an organic solvent at a temperature of $-10°$ to $+40°$ C. for 0.5-10 hours to give an ether amic acid. Second, the ether amic acid is subjected to ring closing dehydration to form imide rings. U.S. Pat. No. 4,460,783 is incorporated here by reference.

The following scheme sets forth the possible polymerization reactions of maleimide.

FIG. 3 shows a melting temperature of about 162° C. and a reaction exotherm of about 239° C.

FIG. 4 is a DSC of a 1:1 molar ratio mixture of bis-2,2-(N-4-benzocyclobutenyl phthalimido)hexafluoro-

POLYMERIZATION REACTIONS OF MALEIMIDE

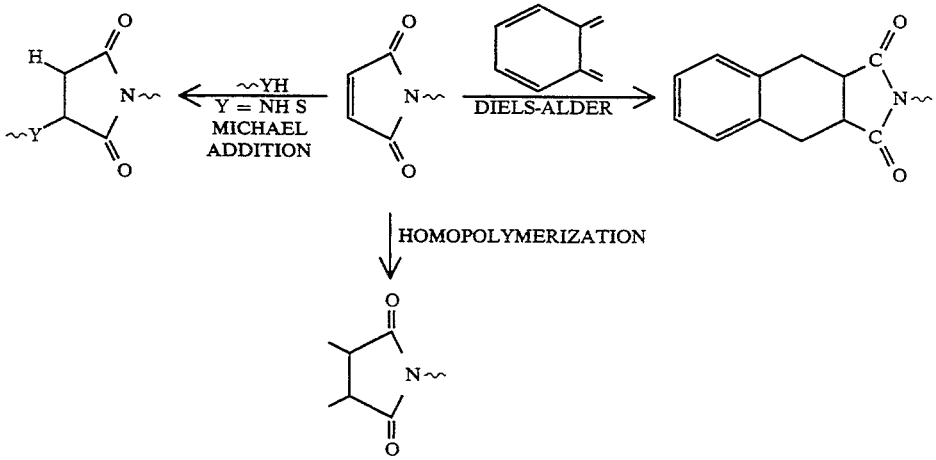

As the scheme indicates, the maleimide functionality can react with a variety of nitrogen or sulfur nucleophiles in Michael-Addition fashion. Such an addition reaction is, in fact, the chemical basis of Kerimid (trade name) and related thermosetting resins. The maleimide functionality is also capable of homopolymerization. The maleimide functionality is also well-known to possess dienophilicity. The dienophilic site, i.e., the carbon-carbon double bond, is not subjected to the substituent effect imposed by the rest of the structure. The maleimide functionality is ideal for Diels-Alder polymerization.

The present invention provides resin blends of compounds of the formula (I) with bis-maleimides of the formula (VII) which are useful in providing reaction products by Diels-Alder polymerization. Upon heating the bis-benzocyclobutene compounds to about 200° C., Diels-Alder polymerization occurs whereby the benzocyclobutene unit undergoes an electrocyclic ring-opening to form the more reactive o-xylylene functionality wherein the o-xylylene functionality undergoes cycloaddition with the maleimide functionality. Homopolymerization of the maleimide functionality and the bis-benzocyclobutene functionality can occur simultaneously with the Diels-Alder polymerization. However, in preparing the resins, the Diels-Alder polymerization should occur at a substantially greater rate than the homopolymerization of the maleimide functionality or the bis-benzocyclobutene functionality in order to maximize the thermal stability of the resins. In general, Diels-Alder polymerization occurs at a temperature of about 200° to 250° C. while homopolymerization occurs at a temperature of about 185° to 240° C.

The resultant resin can be aromatized at high-temperature in the presence of air ($O_2$) to enhance the thermodynamic stability of the final polymeric structure. Although gaseous $H_2O$ will be produced as a volatile by-product, such process will take place primarily on the surface of the thermosets and the adverse effect due to void-formation will be minimal.

FIG. 3 is a DSC of 1,1'-(methylene di-4,1 phenylene)-bis-maleimide. The scan rate was 10° C. per minute.

propane and 1,1-(methylene di-4,1-phenylene)bis-maleimide. FIG. 4 shows a Tpoly max of about 259° C. The complete compatibility is evidenced by a single Tg. At about 259° C., Diels-Alder polymerization predominates over homopolymerization of the maleimide or bis-benzocyclobutene functionality because the reaction sites are much more reactive toward Diels-Alder polymerization than homopolymerization. The Diels-Alder polymerization occurs at a substantially faster rate so that the Diels-Alder polymerization product is favored.

Table 3 sets forth thermal properties of compatible mixtures of bis-2,2-(N-4-benzocyclobutenyl phthalimido)hexafluoropropane (BCB) and 1,1'-(methylene di-4,1-phenylene)bis-maleimide (BMI):

TABLE 3

THERMAL CHARACTERISTICS OF COMPATIBLE MIXTURES OF BIS-2,2-(N-4-BENZOCYCLOBUTENYL PHTHALIMIDO) HEXAFLUOROPROPANE (BCB) AND 1,1'-(METHYLENE DI-4,1-PHENYLENE)BIS-MALEIMIDE (BMI)

| MOLAR RATIO | | $T_{g(ini)}$ | $T_m$ | $T_{poly}$ | | Tg (cure) | $T_{10\%}$ (Air) |
|---|---|---|---|---|---|---|---|
| BCB | BMI | | | Onset | Max. | | |
| 1 | 0 | 116 | 219 | 232 | 258 | 281[b] | 496 |
| 0 | 1 | — | 162 | 185 | 239 | —c | 492 |
| 1 | 1 | 61 | — | 224 | 259 | 293[a] | 500 |
| 1 | 1.5 | 68 | — | 221 | 257 | 298[a] | 520 |
| 1 | 3 | 70 | — | 225 | 257 | —c | 492 |
| 1.5 | 1 | 68 | — | 222 | 257 | 298[a] | 515 |

All Table 3 temperature values are expressed in °C. Tg(ini) is the initial glass transition temperature while Tm is the melting temperature. Tpoly onset is the beginning polymerization temperature while Tpoly max is the temperature at which polymerization reaches its maximum. Tg(cure) is the glass transition temperature of the cured mixture. Tg(cure) was determined by both DSC analysis (value a) and by thermomechanical analysis (value b) which employ a sensitive probe to detect the softening of the sample at its surface. Value c indicates that Tg(cure) was not observed by DSC. Because Tg(cure) relates to the cured material, all samples were cured at 250° C. under $N_2$ atmosphere for 8 hours. $T_{10\%}$ air is the temperature at which a 10% weight loss was observed by thermal gravimetric analysis.

FIG. 5 represents isothermal aging studies of cured mixtures of BCB and BMI. The samples were cured as indicated above for Tg(cure). The isothermal aging studies were carried out by placing cured samples in a circulating air oven at 343° C. for 200 hours, and periodically measuring the change in weight. The cured BMI sample was almost completely vaporized whereas all mixtures exhibited similar thermooxidative stabilities to BCB. This data illustrates the high temperature utility of the resins.

The cure mechanism for the bis-benzocyclobutene-bis-maleimide systems has a significant impact on the nature and properties of the resins prepared. In a preferred embodiment, the resins are useful in composite materials in the advanced aircraft and aerospace vehicles.

Dicyanates useful in the present invention can be prepared by using fully conventional methods. For example, dicyanates can be readily obtained from any compound containing two phenolic groups and cyanogen chloride or cyanogen bromide in the presence of an acid acceptor. The reaction is summarized as follows:

H—O—Ar—O—H + BrC≡N + 2($CH_3CH_2$)$_3$N
→N≡C—O—Ar—O—C≡N + 2($CH_3CH_2$)$_3$NHBr

Dicyanates are useful bisdienopniles because they are inexpensive. The cyanate functionality with its carbon-nitrogen triple bond is known to possess dienophilicity and is ideal for Diels-Alder polymerization. Although monomeric dicyanates can be cured thermally after B-staging, the curing time is much shorter when a catalyst is used. Solutions of transition metal carboxylates in liquid hydrophobic alcohol or alkylated phenol carriers, e.g., benzyl alcohol or nonylphenol, are typical catalyst packages. A typical transition metal carboxylate is copper naphthenate.

During cure, the monomeric dicyanates undergo cyclotrimerization to form a network structure with triazine or cyanurate rings at the crosslinking junctures. As disclosed by Shimp, "The Translation of Dicyanate Structure and Cyclotrimerization Efficiency to Polycyanurate Properties," *Proceedings of the American Chemical Society, Polymeric Materials: Science and Engineering Division*, 54, 107(1986), the following scheme sets forth the trimerization of dicyanate monomers wherein the trimerization is catalyzed by transition metal carboxylates and active hydrogens:

TRIMERIZATION CATALYZED BY TRANSITION
METAL CARBOXYLATES
AND ACTIVE HYDROGENS

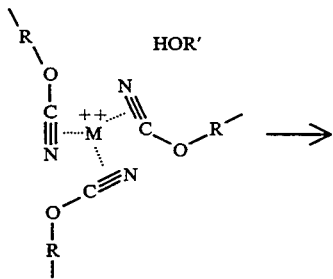

-continued
TRIMERIZATION CATALYZED BY TRANSITION
METAL CARBOXYLATES
AND ACTIVE HYDROGENS

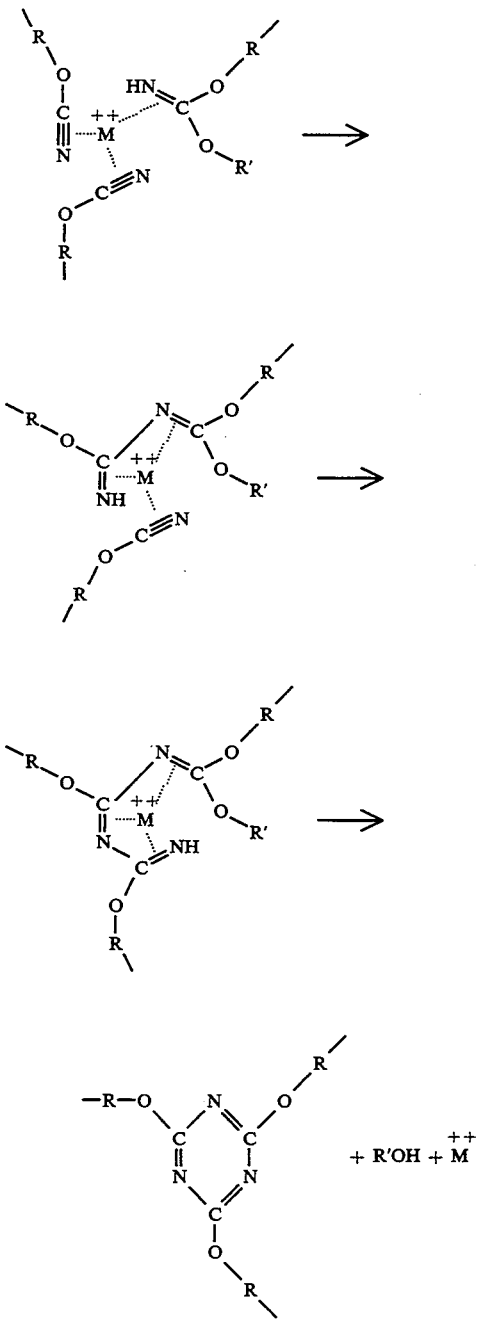

As the scheme indicates, more than one catalyst mechanism appears to operate. The coordination metals appear to gather cyanate groups into ring-forming proximity when molecular mobility is high. Ring closure may proceed by an anion, e.g., octoate, an initiated ionic mechanism (not shown), or by an active hydrogen transfer via the imidocarbonate intermediate as shown. After gelation, active hydrogen catalysts, particularly monohydroxyl compounds, are more efficient than the transition metal ions in achieving a high degree of conversion. A step-growth mechanism involving hydroxyl-initiated chaining via imidocarbonate proton transfer (series of bimolecular collisions) is suggested as the principal cyanate gathering mechanism.

The present invention provides resin blends by Diels-Alder polymerization of compounds of the formula (I) with dicyanates of the formula (VIII). Upon heating the bis-benzocyclobutene compounds to about 200° C., Diels-Alder polymerization occurs whereby the benzocyclobutene unit undergoes an electrocyclic ring-opening to form the more reactive o-xylylene functionality wherein the o-xylylene functionality undergoes cycloaddition with the cyanate functionality. Homopolymerization of the bis-benzocyclobutene functionality and cyclotrimerization of the cyanate functionality, if a catalytic system is present, can occur simultaneously with the Diels-Alder polymerization. However, in preparing the resin blends, the Diels-Alder polymerization should occur at a substantially greater rate than the homopolymerization of the bis-benzocyclobutene functionality in order to maximize the thermal stability of the resin blends. Because dicyanate monomers undergo homopolymerization via a cyclotrimerization mechanism at temperatures as low as about 177° C. in the presence of a catalytic system such as a transition metal carboxylate and a nonvolatile phenol and because bis-benzocyclobutene does not react below about 200° C., preferably, a catalytic system is not used in order to prevent the dicyanate monomers from reacting with each other before they react with bis-benzocyclobutene in a Diels-Alder fashion.

FIG. 6 is a DSC of a 1:1 molar ratio mixture of 2,2-bis[4-(N-4-benzocyclobutenyl phthalimido)]hexafluoropropane with bisphenol A dicyanate. The DSC was run at a heating rate of 10° C./minute. FIG. 6 shows a melting temperature of about 172° C. and a reaction exotherm of about 267° C.

Table 4 sets forth thermal properties of 2,2,-bis[4-(N-4-benzocyclobutenyl phthalimido)]hexafluoropropane (BCB); dicyanates; and their resin blends:

sition occurs as observed by TGA. "a" indicates that only decomposition/volatilization was observed beginning at 234° C. "b" indicates that decomposition (major exothermic process) also occurs. "c" indicates that the samples were previously cured at 200°-220° C./N$_2$/40 hours.

Under DSC conditions of N$_2$ and a scanning rate of 10° C. min., the decomposition processes are occurring at a much faster rate at or near the temperature at which cure is taking place in all the pure dicyanate samples. Both BADCy and THIOCy showed small exotherms (onset at 277° C. and 226° C., and peak at 308° C. and 289° C., respectively). Their major decompositions began at about 251° C. and 246° C., respectively.

On the contrary, all the 1:1BCB/dicyanate blends displayed the expected thermal transitions. Besides initial Tg's (20°-28° C.) and Tm's (171°-183° C.), all samples showed small exotherms in their DSC scans with maxima at 147°-151° C. which is attributable to the thermally-induced crystallization in the mixtures which also led to some initial phase separation. The polymerization exotherms are consistent with the typical temperature ranges for the known benzocyclobutene-based systems (onset: 229°-233° C.; 259°-268° C.).

For comparative isothermal aging studies, all samples of pure BCB and the dicyanate monomers as well as their 1:1 molar mixtures were cured in a single batch at 200°-220° C. for 40 hours under nitrogen atmosphere. The cured BCB sample was translucent and yellow. The cured BADCy, METHYLCy, and THIOCy samples were all transparent and yellow/amber, and their blends with BCB were also transparent but dark red in color.

Figure 7:
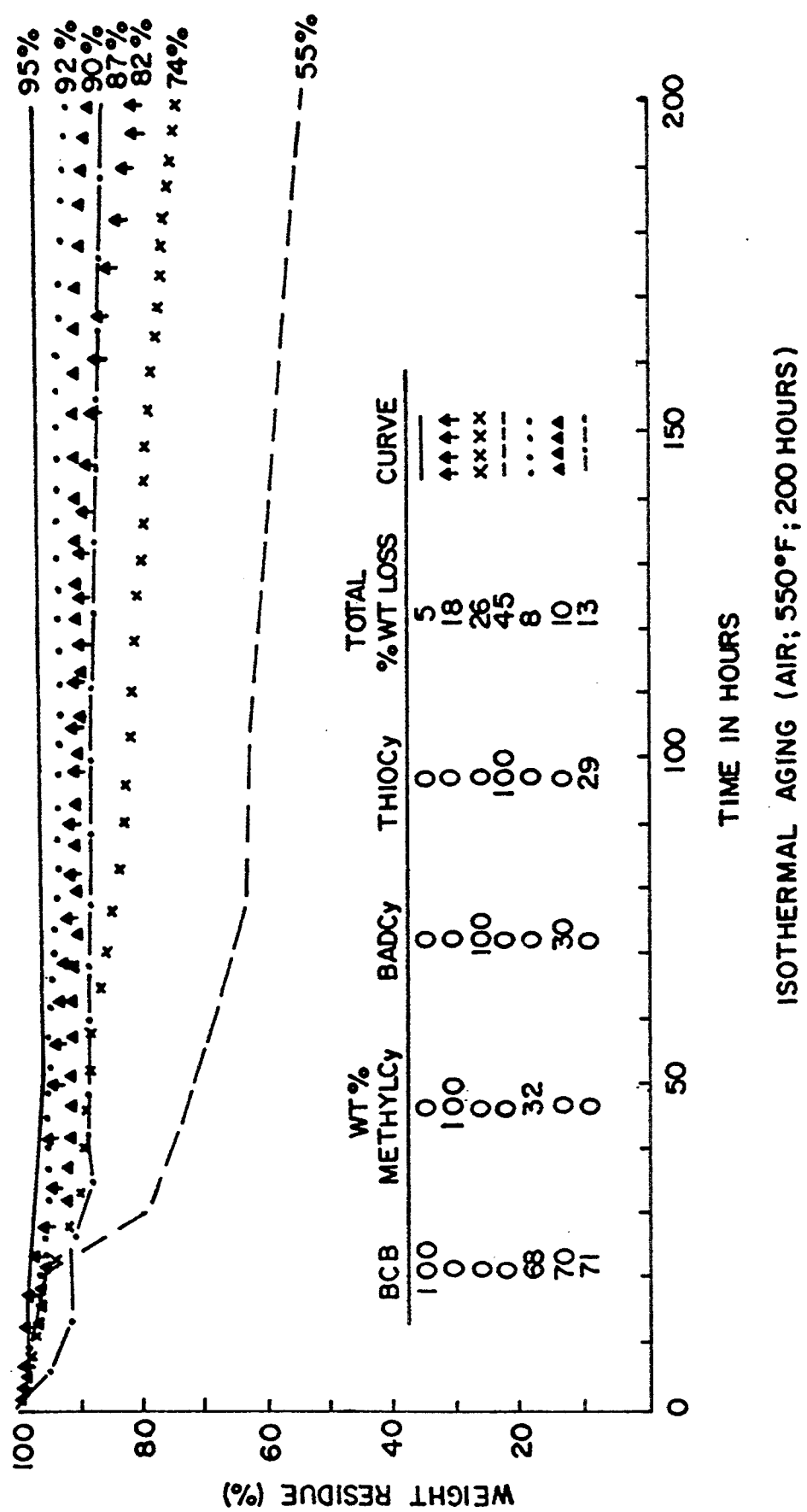
FIGS. 7 and 8 provide isothermal aging studies for 2,2-bis[4-(N-4-benzocyclobutenyl phthalimido)]hexafluoropropane; bisphenol A dicyanate; tetramethylbisphenol F dicyanate; thiodiphenol dicyanate; and blends prepared therefrom.

The ITGA results at 288° C. of the cured samples of BCB, the dicyanate monomers, and BCB/dicyanate blends are depicted graphically in FIG. 7. After 200 hours of isothermal aging at 288° C. in an atmosphere of circulating air, the dicyanate-based thermosets had re-

TABLE 4

THERMAL CHARACTERISTICS OF BCB, DICYANATES AND THEIR BLENDS (1:1)

| COMPOSITION | $T_g$ (ini.) | $T_c$ | $T_m$ | $T_{poly}$ | | $T_g$ (cure) | | $T_d$ |
|---|---|---|---|---|---|---|---|---|
| | | | | ONSET | MAX | DSC | TMA | |
| METHYLCy | — | — | 110 | —a | —a | — | 224$^c$ | 255 |
| BADCy | — | — | 84 | 277 | 308$^b$ | — | 245$^c$ | 251 |
| THIOCy | — | — | 98 | 226 | 289$^b$ | — | 261$^c$ | 246 |
| BCB | 161 | — | 219 | 230 | 258 | 281 | — | 470 |
| BCB/METHYLCy | 27 | 151 | 183 | 233 | 268 | 215 | 255$^c$ | 427 |
| BCB/BADCy | 28 | 147 | 171 | 233 | 266 | — | 269$^c$ | 404 |
| BCB/THIOCy | 20 | 148 | 181 | 229 | 259 | 232 | 271$^c$ | 392 |

All Table 4 temperature values are expressed in °C. The blends are in a 1:1 molar ratio. Unless otherwise specified, all data were obtained from the analyses of samples without prior cure. METHYLCy is tetramethyl bisphenol F dicyanate. BADCy is bisphenol A dicyanate while THIOCy is thiodiphenol dicyanate. Tg(ini) is the initial glass transition temperature. Tc is the maximum temperature at which crystallization from the amorphous phase, i.e., possible phase separation, occurs while Tm is the melting temperature. Tpoly onset is the beginning polymerization temperature while Tpoly max is the temperature at which polymerization reaches its maximum. Tg(cure) is the glass transition temperature of the cured mixture. Tg(cure) was determined by both DSC analysis and by thermomechanical analysis which employs a sensitive probe to detect the softening of the sample at its surface. Td is the extrapolated temperature at which major decomposition.

tained only 55-82% of their original weight. Under the same conditions, the BCB/dicyanate mixtures had retained 87-92% of their original weights as opposed to 95% weight retention observed for pure BCB. It is evident that at 288° C., the blend systems possess thermooxidative stability (87-92% weight retention) comparable to that of BCB (95% weight retention). Thus, instead of using 100% BCB for a 288° C. application, a blend system of BCB and METHYLCy (68%/32%) can be used to lower the cost because METHYLCy is much less expensive than BCB to manufacture.

Figure 8:
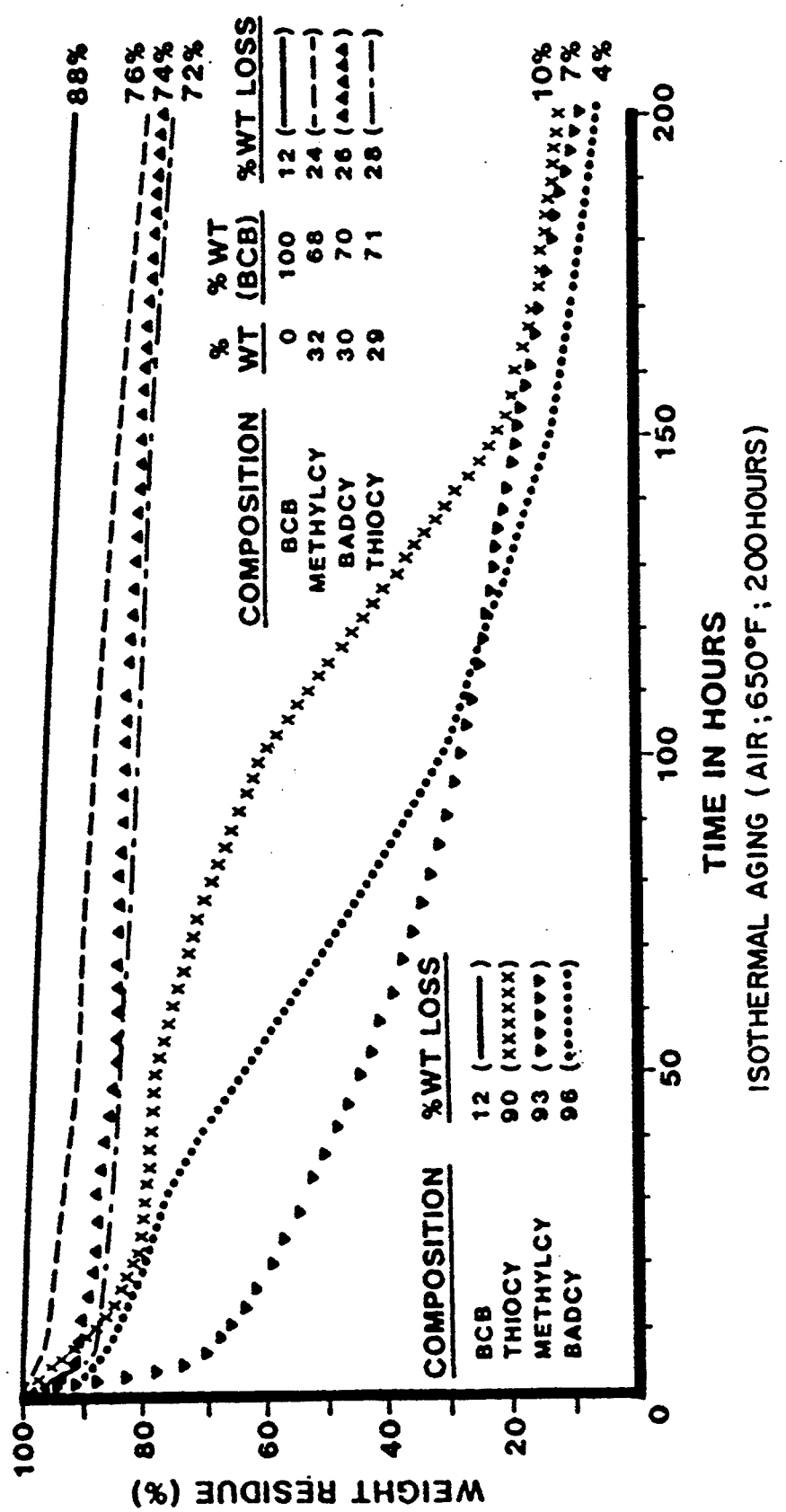

The ITGA results at 353° C. of the cured samples of BCB, the dicyanate monomers, and BCB/dicyanate blends are depicted graphically in FIG. 8. After 200 hours of isothermal aging at 353° C. in an atmosphere of circulating air, the dicyanate-based thermosets had retained only 4–10% of their original weight. Under the same conditions, the BCB/dicyanate mixtures had retained 72–76% of their original weights as opposed to 88% weight retention observed for pure BCB.

Bisphenylacetylenes useful in the present invention can be prepared by using fully conventional methods. A two-step synthesis of 1,1′-(1,3-phenylene)bis-(3-phenyl-2-propyn-1-one) has been reported in Bass et al., *Am. Chem. Soc. Polym. Div. Polym. Preprints* 27(1), 313(1985) and Sinsky et al, *J. Poly. Sci. Part A: Poly. Chem.* 24, 2279(1986). It has been found that 1,1′-(1,3-phenylene)-bis-(3-phenyl-2-propyn-1-one) can be prepared from a one-step route by starting from isophthaloyl chloride and phenylacetylene and employing $PdCl_2(PPh_3)_2$ CuI as the catalytic system, triethylamine as the solvent, and HCl acceptor in 40–50% yield.

2,2-bis[4-(N-3-phenylethynyl)phthalimido]hexafluoropropane can be prepared from 3-aminotolan and 2,2-bis(4-phthalimido)hexafluoropropane in N,N-dimethylacetamide using acetic anhydride/pyridine as the cyclodehydrating agent. 3-aminotolan can be obtained from sodium hydrosulfite reduction of 3-nitrotolan which can be prepared from the coupling reaction of copper (I) phenylacetylide with 3-bromonitrobenzene.

The phenylacetylene functionality with its carbon-carbon triple bond is known to possess dienophilicity and is ideal for Diels-Alder polymerization. The phenylacetylene group is also capable of homopolymerization.

The present invention provides resin blends by Diels-Alder polymerization of compounds of the formula (I) with bisphenylacetylenes of the formula (XI). Upon heating the bis-benzocyclobutene compounds to about 200° C., Diels-Alder polymerization occurs whereby the benzocyclobutene unit undergoes an electrocyclic ring-opening to form the more reactive o-xylylene functionality wherein the o-xylylene functionality undergoes cycloaddition with the phenylacetylene functionality. Homopolymerization of the bis-benzocyclobutene functionality and the phenylacetylene functionality can occur simultaneously with the Diels-Alder polymerization. However, in preparing the resin blends, the Diels-Alder polymerization should occur at a substantially greater rate than the homopolymerization of the bis-benzocyclobutene and phenylacetylene functionalities in order to maximize the thermal stability of the resin blends.

FIG. 9 is a DSC of a 1:1 molar ratio mixture of 2,2-bis[4-(N-4-benzocyclobutenyl phthalimido)]hexafluoropropane with 1,1′-(1,3-phenylene)bis-(3-phenyl-2-propyn-1-one). A single low initial Tg of about 38.3° C. was observed which indicates the compatibility of the components. A polymerization exotherm with an onset of about 217° C. and a maximum of about 264° C. was observed. A small overlapping exotherm peaking at 308° C. was also observed and was probably due to the simultaneous occurrence of the homopolymerization and decomposition of the residual 1,1′-(1,3-phenylene)-bis-(3-phenyl-2-propyn-1-one).

Table 5 sets forth thermal properties of 2,2-bis[4-(N-4-benzocyclobutenyl phthalimido)]hexafluoropropane (BCB); 2,2-bis[4-(N-3-phenylethynyl)phthalimido]hexafluoropropane (PhATI); 1,1′-(1,3-phenylene)bis-(3-phenyl-2-propyn-1-one) (1,3,-PPPO); and their resin blends:

TABLE 5

THERMAL PROPERTIES OF BCB, PhATI, 1,3,-PPPO AND OTHER BLENDS (1:1)

| COMPOSITION | $T_g$ (ini.) | $T_m$ | $T_{poly}$ ONSET | $T_{poly}$ MAX | $T_g$ (cure) | $T_d$ | TGA $T_{10\%}$ Loss | ITGA % Wt. |
|---|---|---|---|---|---|---|---|---|
| BCB | 161 | 219 | 230 | 259 | 281a | 470 | 500 | 12 |
| PhATI | 111 | — | 305 | 370 | 358$^a$ (202)$^{b,c}$ | 460 | 540 | 16 |
| 1,3-PPPO | — | 118 | 266 | 312 | 270$^b$ | 264 | 298 | 84 |
| BCB/PhATI | 96 | — | 230 312 | 268 367 | 250 (264)$^{b,c}$ | 477 | 525 | 9 |
| BCB/1,3-PPPO | 38 | — | 217 | 264 308 | 233 (226)$^b$ | 400 | 508 | 50 |

All Table 5 temperature values are expressed in °C. Tg(ini) is the initial glass transition temperature while Tm is the melting temperature. Tpoly onset is the beginning polymerization temperature while Tpoly max is the temperature at which polymerization reaches its maximum. Tg(cure) is the glass transition temperature of the cured mixture. Td is the extrapolated temperature at which major decomposition started while T10% is the temperature at which a 10% weight loss was observed. ITGA occurred at 343° C. for 200 hours in circulating air. "a" indicates that the samples were previously cured for eight hours under $N_2$ (250° C. for BCB and 350° C. for PhATI). "b" indicates that the samples were previously cured at 263°–265° C. for 40 hours under $N_2$. "c" indicates that the DSC showed residual exotherms with onset at 312° C. for PhATI and at 340° C. for 1:1 PhATI/BCB.

The present invention is illustrated in more detail by the following non-limiting Examples:

EXAMPLE 1

Preparation of bis-2-2-(N-4-benzocyclobutenyl phthalimido)hexafluoropropane

A mixture of bis-2,2-(4-phthalic anhydrido)hexafluoropropane (4.00 g, 10.1 mmol) and 4-aminobenzocyclobutene (2.40 g, 20.1 mmol) freshly prepared from the catalytic hydrogenation of 4-nitrobenzocyclobutene, were gently refluxed in acetic acid (75 ml) under nitrogen atmosphere overnight. The resultant dark and homogeneous reaction mixture was allowed to cool to room temperature and poured into 300 ml of $H_2O$. Immediately, precipitation of gray solids occurred, which could be extracted into ethyl ether (100 ml., then 3×50 ml). The ethereal extract was then washed with aqueous sodium carbonate and dried over magnesium sulfate. Subsequent removal of the solvent by rotary evaporation led to the isolation of about 5.5 g of crude dark brown product, which was subjected to the following chromatographic purification. The crude product was dissolved in about 20 ml of methylene chloride and added to a quartz column (internal diameter: 2.0 cm)

containing about 120 g of silica gel and saturated with petroleum ether. Elution with 1:1 ether/petroleum ether resulted in the collection of light yellow solution as first fractions, which upon standing at room temperature, gradually deposited light yellow needles. The product was collected, washed with petroleum ether and dried in an oven at 100° C. for about an hour. Yield: 3.78 g (57.8%). mp=216°–216.5° C. Calc. for $C_{35}H_{20}F_6N_2O_4$: 65.02% C; 3.12% H; 4.33% N. Found: 65.07% C; 3.23% H; 4.18% N. Mass spectroscopy: M/e=646 (M+) 30.7%. Proton NMR (CDCl$_3$): 3.26 (singlet, alicyclic protons): 7.07–7.30, 7.85–8.18 (complex, aromatic protons). IR (KBr Pellet): 2968W, 2925W (alicyclic C—H stretches); 1778M, 1717 vs (imide group stretches); 1243s, 1188s (asymmetric and symmetric stretches of —C(CF$_3$)$_2$— group).

EXAMPLE 2

Preparation of 2,2-bis[4(N-4'-benzocyclobutenyl-4''-phenoxyphthalimido)]hexafluoropropane A mixture of 1.63 g (13.7 mmol) of freshly prepared 4-aminobenzocyclobutene and 4.00 g (6.36 mmol) of 2,2-bis[4-(3,4-dicarboxyphenoxy)phenyl]hexafluoropropane dianhydride (BFDA) was heated to reflux in acetic acid (60 ml) under N$_2$. The reaction mixture became homogeneous and dark upon reflux, which was maintained for about 17 hrs. The dark reaction mixture was allowed to cool to room temperature and poured into about 350 ml of distilled water. Extraction was subsequently conducted using methylene chloride (100 ml, then 3×50 ml) as the extracting solvent. The organic extract was then washed with aqueous sodium carbonate and saturated sodium chloride solution, and finally dried over magnesium sulfate. The resultant solution was concentrated on a rotary evaporator until its volume was about 50 ml, and subjected to chromatographic purification. (350 g silica gel saturated with hexane; 1:1 CH$_2$Cl$_2$/hexane as eluent.) The desired product was obtained, after the removal of solvent from the first fractions, as light yellow microcrystalline solid. Yield: 3.74 g (67.8%). mp=128°–132° C. Calc. for $C_{47}H_{28}F_6O_6N_2$: 67.94% C; 3.40% H; 3.37% N. Found: 67.99% C; 3.76H; 3.19% N. Mass spectroscopy: 830(M++, 2%); 415 (M+++, 6%). Proton NMR (CDCl$_3$): 3.23 (singlet, all cyclic protons); 7.06–8.03 (complex, aromatic protons). IR (KBr pellet): 2922W, 2960VW (alicyclic C—H stretches); 1714 vs, 1771m (imide group stretches); 1202 m, 1235s (symmetric and asymmetric stretches of —C(CF$_3$)$_2$— group); 1168 ms (Ar—O—Ar stretch).

EXAMPLE 3

Preparation of bis[4(N-4'-benzocyclobutenyl-4''-phenoxyphthalimido)] Sulfone

A mixture of 4-aminobenzocyclobutene (0.75 g, 6.29 mmol) and 1,4-bis(3,4-dicarboxyphenoxy)diphenylsulfone dianhydride (BSDA) (1.50 g, 2.96 mmol) was refluxed in acetic acid (55 ml) under N$_2$ overnight. The resultant dark reaction mixture was allowed to cool to room temperature and poured into 300 ml of distilled water. The crude product was then extracted into methylene chloride (100 ml, then 3×50 ml) and the organic extract was subsequently treated with aqueous 10% sodium bicarbonate and saturated sodium chloride solution. After having been dried over magnesium sulfate, the methylene chloride extract was concentrated on a rotary evaporator until its volume was about 35–40 ml. Subsequent chromatographic purification (300 g silica gel saturated with petroleum ether; 1:1 methylene chloride/petroleum ether as the eluting solvent) led to the isolation of the desired product, which was obtained from the first fractions as light yellow microcrystalline solid. Yield: 1.18 g (53.6%). mp=245°–246° C. Calc. for $C_{44}H_{28}N_2O_8S$: 70.96% C; 3.79% H; 3.76% N. Found: 70.81% C; 3.99% H; 3.64% N. Proton NMR (CDCl$_3$): 3.25 (singlet, alicyclic protons); 7.09–7.54, 7.96–8.16 (complex, aromatic protons). IR (KBr pellet): 3060 VW, 3085 VW (aromatic C—H stretches); 2930 W, 2965 VW (alicyclic C—H stretches); 1700 VS; 1764 ms (imide group stretches); 1232 VS, 1372 VS (symmetric and asymmetric stretches of —SO$_2$— group); 1089 ms, 1102 ms (Ar—O—Ar stretches).

EXAMPLE 4

Compound prepared from bis-2,2-(4-phthalic anhydrido)hexafluoropropane; 2,2'-bis(3-aminophenyl)hexafluoropropane; and 4-aminobenzocyclobutene 4.08 g (9.18 mmol) of bis-2,2-(4-phthalic anhydrido)hexafluoropropane suspended under N$_2$ in acetic acid (100 ml)/toluene (80 ml) was heated to about 65° C., at which temperature all the dianhydride dissolved. 2,2'-bis(3-aminophenyl)hexafluoropropane (1.50 g. 4.49 mmol) was subsequently added neat in small portions over a period of 20 minutes, at which the temperature of the reaction mixture was maintained at 70°–80° C. The resultant yellow homogeneous reaction mixture was then heated to reflux and the water of condensation was collected azeotropically. After an overnight reflux, the yellow reaction was allowed to cool to about 40° C. and freshly prepared 4-aminobenzocyclobutene (2.80 g, 23.5 mmol) in about 10 ml of toluene was added. Reflux of the reaction mixture was resumed and continued for another 30 hrs under N$_2$. The dark reaction mixture was allowed to cool to room temperature and poured into 600 ml of distilled water. Extraction was performed using ethyl acetate as the extracting solvent (100 ml, then 3×50 ml). The organic extract was then washed with 10% aqueous sodium bicarbonate (500 ml) and then distilled water (2×500 ml). After having dried over magnesium sulfate, the organic extract was subjected to rotary evaporation to remove all the solvent. The fluffy gray crude product was then dissolved in methylene chloride and the resultant solution was filtered through a bed of silica gel (40 g), washing with methylene chloride until the filtrate was almost colorless. The yellow filtrate was rota-evaporated to remove about half the volume of the solvent. Hexane was added to gradually precipitate out light tan microcrystalline solid. The solvents were further removed and the product was finally collected, washed with hexane, and dried in vacuo at approximately 60° C. for two days. Yield=7.60 g.

Another batch of the oligomer was prepared similarly except for the purification step. Thus, 5.75 g (12.94 mmol) of bis-2,2-(4-phthalic anhydrido)hexafluoropropane, 2.06 g (6.16 mmol) of 2,2-bis(3-aminophenyl)hexafluoropropane and 3.84 g (32.23 mmol) of 4-aminobenzocyclobutene were reacted in 150 ml acetic acid/200 ml toluene mixture. After the usual work-up as described above, the crude product was dissolved in a minimal amount of methylene chloride and the resultant solution was passed through a small column containing about 20 g of silica gel. The column was then eluted with methylene chloride until all fluorescent material was collected. Removal of the solvents from the fractions collected led to the isolation of 8.04 g of yellow microcrystalline solid as the pure product.

EXAMPLE 5

Compound prepared from bis-2,2-(4-phthalic anhydrido)hexafluoropropane oxydianiline and 4-aminobenzocyclobutene 5.75 g (12.94 mmol) of bis-2,2-(4-phthalic anhydrido)hexafluoropropane, 1.30 g (6.49 mmol) of oxydianiline and 3.70 g (31.0 mmol) of 4-aminobenzocyclobutene were reacted in 200 ml acetic acid/100 ml toluene. The crude product was dissolved in approximately 100 ml methylene chloride, after the usual work-ups as described above. The resultant solution was then passed through a small column containing about 50 g silica gel, using hexane as the eluting solvent. The desired product was obtained from the first fractions as amber microcrystalline solid. Yield: 6.40 g.

EXAMPLE 6

Compound prepared from bis-2,2-(4-phthalic anhydrido)hexafluoropropane p-phenylenediamine and 4-aminobenzocyclobutene 5.75 g (12.94 mmol) of bis-2,2-(4-phthalic anhydrido)hexafluoropropane, 0.80 g (7.40 mmol) of p-phenylenediamine and 3.60 g (30.21 mmol) of 4-aminobenzocyclobutene were reacted in 200 ml acetic acid/100 ml toluene. The crude product was dissolved in about 30 ml of methylene chloride and the resultant solution was passed through a small column containing 50 g of silica gel saturated with petroleum ether, which was also used as the eluting solvent. The desired product was a golden microcrystalline solid. Yield: 4.60 g.

EXAMPLE 7

Compound prepared from bis-2,2-(4-phthalic anhydrido)hexafluoropropane; m-phenylenediamine; and 4-aminobenzocyclobutene 3.79 g (8.53 mmol) of bis-2,2-(4-phthalic anhydrido)-hexafluoropropane, 0.45 g (4.16 mmol) of m-phenylenediamine (purified Dy washing it with acetone in a fritted filter funnel until colorless crystals were obtained) and 1.10 g (9.23 mmol) of 4-aminobenzocyclobutene was reacted in 120 ml acetic acid/60 ml toluene at 110° C. as described above. After the usual work-up, the crude product was dissolved in about 100 ml of methylene chloride and filtered through a bed of silica gel (50 g) on a fritted filtered funnel, washing with methylene chloride until the filtrate was almost colorless. Removal of the solvent from the yellow filtrate led to the isolation of the desired product as a light tan microcrystalline solid. Yield: 3.20 g.

EXAMPLE 8

Preparation of Intimate Bis-2,2 (N-4-benzocyclobutenyl phthalimido)hexafluoropropane and 1,1'-(Methylene di-4-,1-phenylene)bis-maleimide mixtures 1,1'-(Methylene di-4,1-phenylene)bis-maleimide was purchased and purified by passing it through $CH_2Cl_2$ solution, through a bed of $SiO_2$ and followed by subsequent rotary evaporation. Calc. for $C_{21}H_{14}N_2O_4$; 70.38% C, 3.94% H, 7.82% N. Found: 69.95% C, 3.99% H, 7.65% N.

0.1709 g ($1.669 \times 10^{-4}$ mol) of Bis-2-2(N-4-benzocyclobutenyl phthalimido)hexafluoropropane and 0.0523 g ($1.675 \times 10^{-4}$ mol) of 1,1'-(Methylene di-4,1-phenylene)bis-maleimide were dissolved completely in about 8 ml of $CH_2Cl_2$. The resultant solution was slowly evaporated to dryness with the assistance of a heat-gun. The mixture was then dried in an oven at 90° C. in vacuo for 48 hrs.

EXAMPLE 9

Preparation of 1:1 molar mixture of 2,2-bis[4-(N-4-benzocyclobutenyl phthalimido)]hexafluoropropane and bisphenol A dicyanate 1.2378 g of 2,2-bis[4-(N-4-benzocyclobutenyl phthalimido)]hexafluoropropane and 0.5328 g of bisphenol A dicyanate were completely dissolved in about 10 ml of methylene chloride. The resultant yellow solution was then heated carefully with a heat gun to remove the solvent. The final yellow viscous liquid was subsequently heated in an oven at about 70°–80° C. for about 15 minutes and vacuum dried at about 50° C. overnight. The mixture was a yellow glassy solid.

EXAMPLE 10

Preparation of 1:1 molar mixture of 2,2-bis[4-(N-4-benzocyclobutenyl phthalimido)]hexafluoropropane and tetramethyl bisphenol F dicyanate 0.6460 g of 2,2-bis[4-(N-4-benzocyclobutenyl phthalimido)]hexafluoropropane and 0.3060 g of tetramethyl bisphenol F dicyanate were completely dissolved in about 10 ml of methylene chloride. The resultant yellow solution was then heated carefully with a heat gun to remove the solvent. The final yellow viscous liquid was subsequently heated in an oven at about 70°–80° C. for about 15 minutes and vacuum dried at about 50° C. overnight. The mixture was a yellow glassy solid.

EXAMPLE 11

Preparation of 1:1 molar mixture of 2,2-bis[4-(N-4-benzocyclobutenyl phthalimido)]hexafluoropropane and thiodiphenol dicyanate 1.0460 g of 2,2-bis[4-(N-4-benzocyclobutenyl phthalimido)]hexafluoropropane and 0.4331 g of thiodiphenol dicyanate were completely dissolved in about 10 ml of methylene chloride. The resultant yellow solution was then heated carefully with a heat gun to remove the solvent. The final yellow viscous liquid was subsequently heated in an oven at about 70°–80° C. for about 15 minutes and vacuum dried at about 50° C. overnight. The mixture was a yellow glassy solid.

EXAMPLE 12

Preparation of 1:1 molar mixture of 2,2-bis[4-(N-4-benzocyclobutenyl phthalimido)]hexafluoropropane and 2,2-bis[4-(N-3-phenylethynyl)phthalimido]hexafluoropropane 0.3082 g (0.4767 mmole) of 2,2-bis[4-(N-4-benzocyclobutenyl phthalimido)]hexafluoropropane and 0.3781 g (0.4758 mmole) of 2,2-bis[4-(N-3-phenylethynyl)phthalimido]hexafluoropropane were dissolved in about 10 ml of methylene chloride. After complete dissolution had been achieved, the solvent was slowly evaporated off with the assistance of a heat gun. The resinous mixture was then dried in vacuum at room temperature for about 30 minutes before it was dried at elevated temperature (about 80° C.) for 17 hours. The resultant mixture was a yellow glassy solid.

EXAMPLE 13

Preparation of 1:1 molar mixture of 2,2-bis[4-(N-4-benzocylobutenyl phthalimido)]hexafluoropropane and 1,1′-(1,3-phenylene)bis(3-phenyl-2-propyn-1-one)

0.3382 g (0.5231 mmole) of 2,2-bis[4-(N-4-benzycyclobutenyl phthalimido)]hexafluoropropane and 0.1756 g (0.5252 mmole) of 1,1′-(1,3-phenylene)bis(3-phenyl-2-propyn-1-one) were completely dissolved in about 10 ml of methylene chloride. The resultant yellow solution was subsequently heated with a heat gun to remove almost all the solvent. The final amber oil was then slowly evacuated in a vacuum oven at room temperature to afford a yellow fluffy solid which was eventually dried at about 60° C. under vacuum for 21 hours.

Having described the invention in detail and by reference to preferred embodiments thereof, it will be apparent that modifications and variations are possible without departing from the scope of the invention defined in the appended claims.

What is claimed is:

1. A blend of a compound of the formula

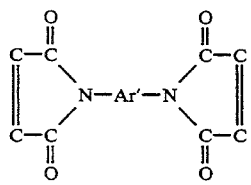

(I)

where R is a divalent linking group, and a bisdienophile, said blending being capable of forming a high temperature resistant thermoset resin.

2. The blend of claim 1 wherein said bisdienophile is a bis-maleimide of the formula:

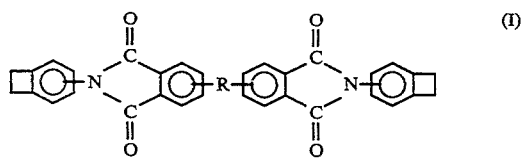

(VII)

where Ar′ is an aromatic linking group.

3. The blend of claim 2 wherein Ar′ is an aromatic linking group such as a linking group selected from the group consisting of a meta phenylene group, a para phenylene group and the formula:

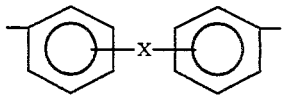

(III)

where X is selected from the group consisting of —C(CF$_3$)$_2$—, —C(CH$_3$)$_2$—, —CH$_2$—, —O—, —S—, —CO—, and —SO$_2$—, or X represents a direct bond.

4. The blend of claim 3 wherein said compound is represented by the formula:

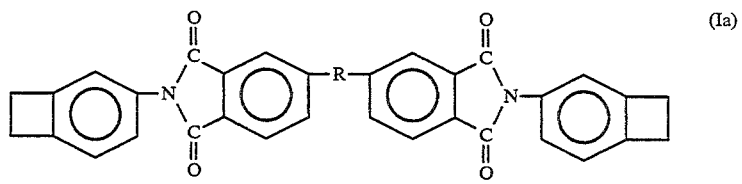

(Ia)

where R is a divalent linking group.

5. The blend of claim 4 wherein said divalent linking group is an aromatic divalent linking group.

6. The blend of claim 4 wherein R is selected from the group consisting of —C(CF$_3$)$_2$—, —(CH$_3$)$_2$—, —CH$_2$—, —O—, —S—, —CO—, and —SO$_2$—, or R represents a direct bond.

7. The blend of claim 5 wherein R is represented by the formula

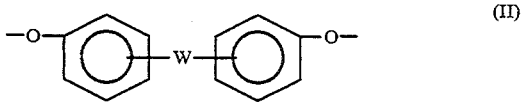

(II)

where W is selected from the group consisting of —C(CF$_3$)$_2$—, —C(CH$_3$)$_2$—, —CH$_2$—, —O—, —S—, —CO—, and —SO$_2$—, or W represents a direct bond.

8. The blend of claim 5 where R is represented by the formula:

(III)

where X is selected from the group consisting of —C(CF$_3$)$_2$—, —C(CH$_3$)$_2$—, —CH$_2$—, —O—, —S—, —CO—, and —SO$_2$—, or X represents a direct bond.

9. The blend of claim 5 wherein R is represented by the formula:

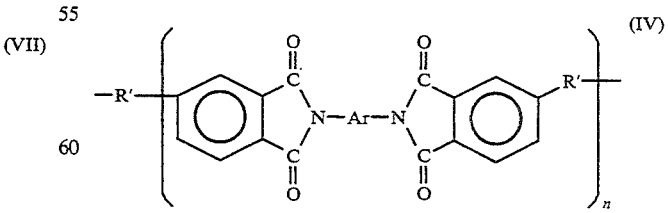

(IV)

where
R′ is selected from the group consisting of —C(CF$_3$)$_2$—, —C(CH$_3$)$_2$—, —CH$_2$—, —O—, —S—, —CO—, and —SO$_2$—, or R′ represents a direct bond, n is 1 to 4, and Ar is selected from the group consisting of a meta phenylene group, a para phenylene group, and the formula:

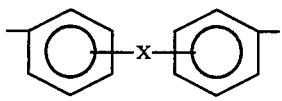

(III)

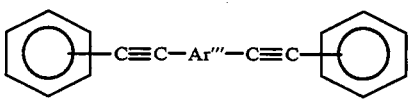

(XI)

where Ar''' is an aromatic linking group.

15. The blend of claim 14 wherein Ar''' is represented by the formula

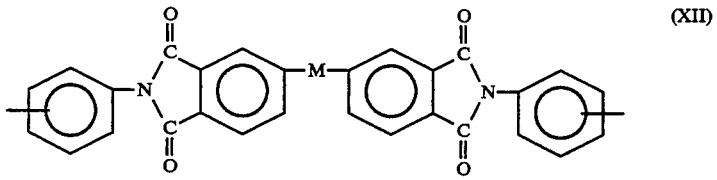

(XII)

where X is selected from the group consisting of —C(CF$_3$)$_2$—, —C(CH$_3$)$_2$—, —CH$_2$—, —O—, —S—, —CO—, and —SO$_2$—, or X represents a direct bond.

10. The blend of claim 1 wherein said bisdienophile is a dicyanate of the formula N≡C—O—Ar''—O—C≡N   (VIII)

where Ar'' is an aromatic linking group.

11. The blend of claim 10 wherein Ar'' is represented by the formula

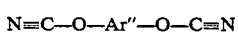

(IX)

where J is selected from the group consisting of —C(CF$_3$)$_2$—, —C(CH$_3$)$_2$—, —CH$_2$—, —O—, —S—, —CO—, and —SO$_2$—, or J represents a direct bond.

12. The blend of claim 10 wherein Ar'' is represented by the formula

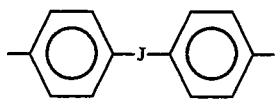

(X)

where L is selected from the group consisting of —C(CF$_3$)$_2$—, —C(CH$_3$)$_2$—, —O—, —S—, —CO—, and —SO$_2$—, or L represents a direct bond.

13. The blend of claim 10 wherein Ar'' is a meta phenylene group.

14. The blend of claim 1 wherein said bisdienophile is a bisphenylacetylene of the formula where M is selected from the group consisting of —C(CF$_3$)$_2$—, —C(CH$_3$)$_2$—, —CH$_2$—, —O—, —S—, —CO—, and —SO$_2$—, or M represents a direct bond.

16. The blend of claim 14 wherein Ar''' is represented by the formula

(XIII)

where Q is selected from the group consisting of ortho phenylene, meta phenylene, or para phenylene.

17. A resin which is a reaction product prepared by polymerization of a compound of the formula:

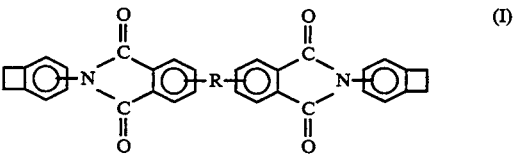

(I)

where R is a divalent linking group.

18. The resin of claim 17 wherein said compound is represented by the formula:

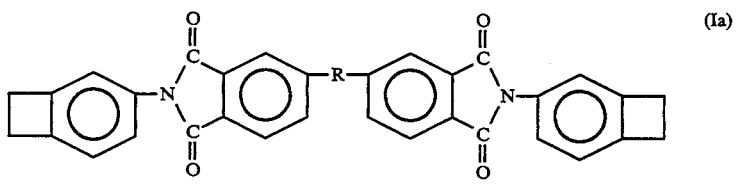

(Ia)

where R is a divalent linking group.

19. The resin of claim 18 wherein said divalent linking group is an aromatic divalent linking group.

20. The resin of claim 18 wherein R is selected from the group consisting of —C(CF$_3$)$_2$—, —C(CH$_3$)$_2$—, —CH$_2$—, —O—, —S—, —CO—, and —SO$_2$—, or R represents a direct bond.

21. The resin of claim 19 wherein R is represented by the formula:

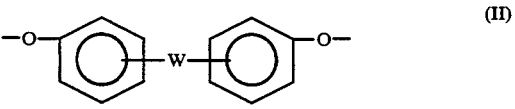

(II)

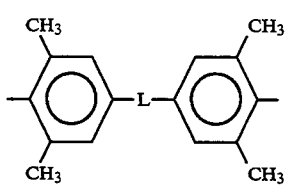

where W is selected from the group consisting of —C(CF$_3$)$_2$—, —C(CH$_3$)$_2$—, —CH$_2$—, —O—, —S—, —CO—, and —SO$_2$—, or W represents a direct bond.

22. The resin of claim 19 wherein R is represented by the formula:

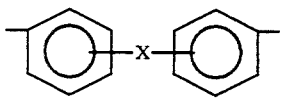
(III)

where X is selected from the group consisting of —C(CF$_3$)$_2$—, —C(CH$_3$)$_2$—, —CH$_2$—, —O—, —S—, —CO—, and —SO$_2$—, or X represents a direct bond.

23. The resin of claim 19 wherein R is represented by the formula:

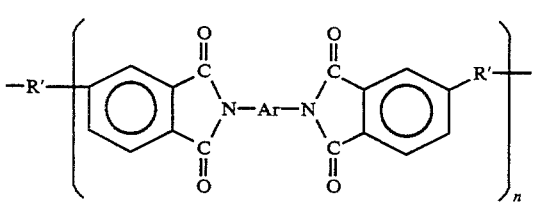
(IV)

where

R' is selected from the group consisting of —C(CF$_3$)$_2$—, —C(CH$_3$)$_2$—, —CH$_2$—, —O—, —S—, —CO—, and —SO$_2$—, or R' represents a direct bond, n is 1 to 4, and Ar is selected from the group consisting of a meta phenylene group, a para phenylene group, and the formula:

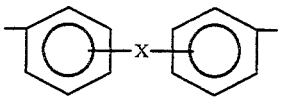
(III)

where X is selected from the group consisting of —C(CF$_3$)$_2$—, —C(CH$_3$)$_2$—, —CH$_2$—, —O—, —S—, —CO—, and —SO$_2$—, or X represents a direct bond.

24. The resin of claim 20 wherein R is —C(CF$_3$)$_2$—.

25. The resin of claim 20 wherein W is —C(CF$_3$)$_2$—.

26. The resin of claim 20 wherein W is —SO$_2$—.

27. A resin which is a reaction product prepared by Diels-Alder polymerization of a compound of the formula:

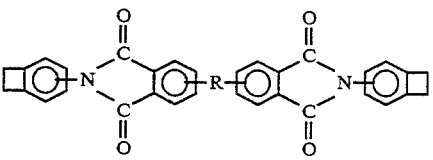

where R is a divalent linking group, and a bisdienophile.

28. A resin which is a reaction product prepared by Diels-Alder polymerization of a bis-benzocyclobutene compound and a dienophile.

29. A resin as recited in claim 28 wherein said dienophile is benzoquinone.

30. A resin as recited in claim 28 wherein said dienophile is a bis-maleimide.

31. A resin which is a reaction product prepared by Diels-Alder polymerization of bis-2,2-(N-4-benzocyclobutenyl pthalimido)hexafluoropropane and 1,1'-(methylene di-4,1-phenylene)bis-maleimide.

32. A copolymer composition comprising, in polymerized form, a comonomer containing two polymerizable arylcyclobutane moieties, and a comonomer containing two polymerizable dienophilic moieties.

33. The copolymer composition of claim 32 wherein the arylcyclobutane moieties are benzocyclobutene moieties.

34. The copolymer composition of claim 33 wherein the dienophilic moieties are maleimide moieties.

* * * * *